(12) United States Patent
Hao

(10) Patent No.: US 12,390,359 B2
(45) Date of Patent: Aug. 19, 2025

(54) THERAPEUTIC ORAL DEVICE

(71) Applicant: 3 Little Ladies, Inc., Jacksonville, FL (US)

(72) Inventor: Phinarak Hao, Jacksonville, FL (US)

( * ) Notice: Subject to any disclaimer, the term of this patent is extended or adjusted under 35 U.S.C. 154(b) by 270 days.

(21) Appl. No.: 18/108,405

(22) Filed: Feb. 10, 2023

(65) Prior Publication Data
US 2023/0190514 A1 Jun. 22, 2023

Related U.S. Application Data

(63) Continuation-in-part of application No. 17/577,734, filed on Jan. 18, 2022, now Pat. No. 11,607,336.
(Continued)

(51) Int. Cl.
| | |
|---|---|
| *A61F 5/56* | (2006.01) |
| *A61B 5/00* | (2006.01) |
| *A61B 5/01* | (2006.01) |
| *A61B 5/0205* | (2006.01) |
| *A61B 5/024* | (2006.01) |

(Continued)

(52) U.S. Cl.
CPC ............ *A61F 5/566* (2013.01); *A61B 5/4818* (2013.01)

(58) Field of Classification Search
CPC ....... A61F 5/566; A61B 5/015; A61B 5/0205; A61B 5/024; A61B 5/087; A61B 5/6812; A61B 5/682; A61B 5/6898; A61B 2562/0219; A61M 16/0495; Y10S 602/902

See application file for complete search history.

(56) References Cited

U.S. PATENT DOCUMENTS

| | | | | |
|---|---|---|---|---|
| 3,132,647 | A * | 5/1964 | Corniello | ................ A61F 5/566 |
| | | | | D24/176 |
| 4,669,459 | A * | 6/1987 | Spiewak | ................ A61F 5/566 |
| | | | | 128/848 |

(Continued)

FOREIGN PATENT DOCUMENTS

| | | | | |
|---|---|---|---|---|
| DE | 10011687 C2 * | 2/2002 | ............... | A61F 5/56 |
| KR | 102361865 B1 * | 2/2022 | | |

(Continued)

*Primary Examiner* — Tarla R Patel
(74) *Attorney, Agent, or Firm* — Camille A. Wilson; Wilson Dutra, PLLC

(57) ABSTRACT

The present disclosure provides generally for a therapeutic oral device for assessing one or more health aspects of a user and/or alleviating one or more health conditions of a user, and associated methods for using the device. According to the present disclosure, the device may comprise a hard palate portion, a mouth guard portion, and a tongue retainer portion. The hard palate portion may comprise one or more materials. The hard palate portion may also comprise a composite of materials, including but not limited to one or more embedded materials. The mouth guard portion may comprise one or more components that provide stability and maintain the position of the therapeutic oral device within the mouth of a user. The tongue retainer portion may comprise an airway and a predetermined length. In some embodiments, the therapeutic oral appliance may comprise one or more electronic components that may be configured to interface with at least one external device. In some aspects, the therapeutic oral appliance may comprise one or more sensors and/or one or more electrodes.

16 Claims, 26 Drawing Sheets

Related U.S. Application Data

(60) Provisional application No. 63/139,051, filed on Jan. 19, 2021.

(51) Int. Cl.
  *A61B 5/087* (2006.01)
  *A61M 16/04* (2006.01)

(56) References Cited

U.S. PATENT DOCUMENTS

| | | | | |
|---|---|---|---|---|
| 5,592,951 | A * | 1/1997 | Castagnaro | A61F 5/566 |
| | | | | 128/862 |
| 5,915,385 | A * | 6/1999 | Hakimi | A61F 5/566 |
| | | | | 128/859 |
| 6,702,765 | B2 | 3/2004 | Robbins | |
| 8,074,656 | B2 | 12/2011 | Vaska | |
| 8,667,970 | B2 * | 3/2014 | Podmore | A61F 5/566 |
| | | | | 128/860 |
| 2003/0078521 | A1 * | 4/2003 | Robbins | A61B 5/4205 |
| | | | | 600/587 |
| 2009/0120447 | A1 * | 5/2009 | Vaska | A61F 5/566 |
| | | | | 128/846 |

FOREIGN PATENT DOCUMENTS

| | | | | |
|---|---|---|---|---|
| WO | WO-9611653 A1 * | 4/1996 | | A61F 5/566 |
| WO | WO-2004021869 A2 * | 3/2004 | | A61F 2/00 |
| WO | WO-2006072147 A1 * | 7/2006 | | A61C 7/065 |

* cited by examiner

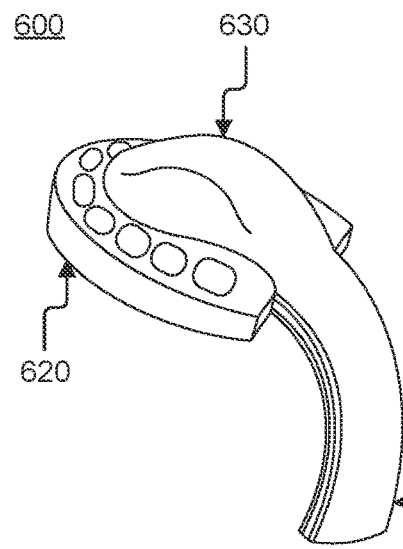
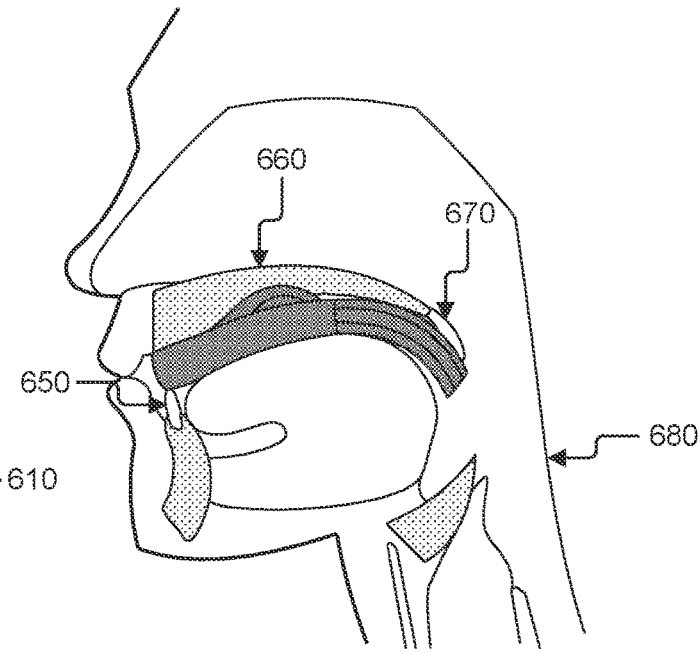
FIG. 6A
FIG. 6B
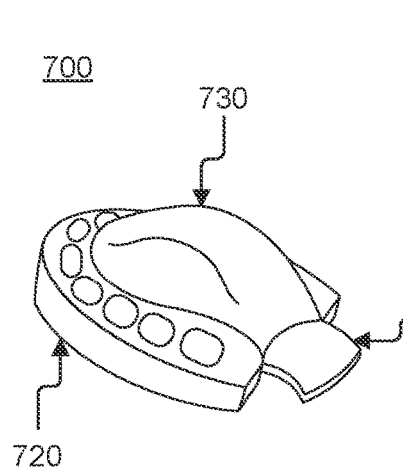
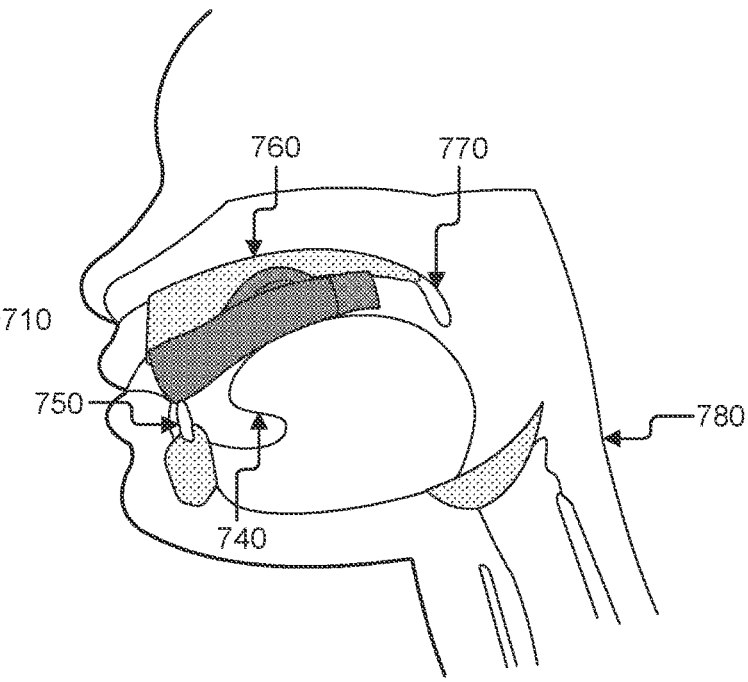
FIG. 7A
FIG. 7B

800

800

1600

1600

THERAPEUTIC ORAL DEVICE

CROSS-REFERENCE TO RELATED APPLICATION

This application is a continuation-in-part and claims priority to and the full benefit of currently pending U.S. Nonprovisional patent application Ser. No. 17/577,734 (filed Jan. 18, 2022, and titled "THERAPEUTIC ORAL DEVICE FOR SLEEP APNEA"), which claims priority to and the full benefit of U.S. Provisional Patent Application Ser. No. 63/139,051 (filed Jan. 19, 2021, and titled "THERAPEUTIC ORAL DEVICE FOR SLEEP APNEA"), the entire contents of which are incorporated in this application by reference.

BACKGROUND

Sleep apnea is a sleeping disorder in which the sleeper's breathing is stopped repeatedly throughout the night. The disorder may cause snoring, restless sleep, difficulty falling asleep or insomnia, excessive sleepiness throughout the day, and more. A number of factors may cause or exacerbate sleep apnea, such as being obese; having a large neck circumference or narrow air passageways; being male; aging; using sedatives, alcohol, or narcotics; and smoking.

There are three types of sleep apnea: obstructive, central, and complex. Obstructive sleep apnea is the most common type and occurs when the throat muscles relax, narrowing the passageway for air to enter or leave. This causes a lack of oxygen flow that alerts the brain and wakes up the sleeper, so that breathing may continue as normal. Although the wake often goes unnoticed by the sleeper because it is so brief, this adds to the restlessness and sleepiness symptoms of the sleeper. Central sleep apnea occurs when the brain fails to transmit signals to the breathing muscles. So rather than a physical obstruction preventing someone from breathing, the sleeper simply makes no effort to breathe and may awaken with shortness of breath. Complex sleep apnea is a combination of obstructive and central.

In addition to the many symptoms of sleep apnea, there may also be long term complications that arise as a result of the disorder. Extreme fatigue may occur, and may not only consist of drowsiness, but may also affect an individual's ability to concentrate, which may affect work performance, increase the risk of workplace or motor vehicle accidents, or cause drastic mood changes. Due to the sudden drops in oxygen levels, the heart may have to work harder than normal, which may increase the chance of high blood pressure, stroke, heart attacks, and more. Furthermore, those with sleep apnea have an increased risk of developing type 2 diabetes. Additionally, sleep apnea may cause complications with standard medications or medical procedures, including surgeries.

Many treatments, devices, and even surgeries have been developed over the years to remedy sleep apnea, though each solution comes with its unique pros and cons. One of the most commonly used treatment devices is the continuous positive airway pressure (CPAP) machine. The CPAP machine requires the sleeper to wear a mask over the nose and mouth, which delivers air at a greater pressure than the surrounding air. This higher air pressure helps the airways stay open, preventing sleep apnea. CPAP machines, however, may be uncomfortable for the wearer, cause claustrophobia or anxiety, and increase the likelihood of dry mouth, nose bleeds, and nasal congestion. Additionally, CPAP machines cost anywhere from $500-$3000, require a prescription, and may not be covered by health insurance.

Other treatments may include wearing an oral appliance, such as a mouthguard or orthodontic retainer, which places pressure on the tongue; nerve stimulation, which sends precise stimuli to nerves in the airway, and nutrition or exercise therapies. Surgery may also work in some instances. This treatment type is most effective for children who get large adenoids or tonsils removed. For adults, it may be difficult to pinpoint what exactly is causing the sleep apnea. Some adult surgical procedures may consist of removing tissue through uvulopalatopharyngoplasty, shrinking tissue with radiofrequency ablation, repositioning the jaw, or implanting rods. Although these procedures may be successful for some, the CPAP machine is still the recommended method of treatment by most physicians.

Being that the mouth and throat are among the main instruments that the body uses to interact with the environment, they can be the site of many health concerns or treatment regimens beyond those associated with sleep apnea. For example, the temperature, air flow, and muscle or jaw movement within the mouth or throat can be indicative of various conditions, particularly when an individual is asleep or under anesthesia. Such conditions often go undiagnosed or misdiagnosed as they are difficult to observe or detect.

SUMMARY OF THE DISCLOSURE

What is needed is a convenient and comfortable way to treat sleep apnea and assess or alleviate other health concerns that is accessible, budget-friendly, and does not cause other health issues. A removable oral appliance with one or more simple electrical components may increase design simplicity. An oral appliance that mimics the basic form of a mouth guard may possess a familiarity through association that enables a user to quickly discern its functionality. The compact nature of an oral appliance that resembles a mouth guard may allow for transportability and compact storage. The removable aspect of the oral appliance may avoid issues of prolonged wear such as tissue necrosis and inflammation.

The present disclosure provides generally for a therapeutic oral device for sleep apnea and other health conditions. According to the present disclosure, the therapeutic oral device may comprise a hard palate portion, a mouth guard portion, and a tongue retainer portion. In some embodiments, the hard palate portion may comprise one or more materials. In some implementations, the hard palate portion may also comprise a composite of materials, including but not limited to one or more embedded materials.

In some aspects, the mouth guard portion may comprise one or more components that provide stability and maintain the position of the therapeutic oral device within the mouth of a user. In some embodiments, the tongue retainer portion may comprise at least one airway and a predetermined length. In some implementations, a method of using the therapeutic oral appliance may comprise the utilization of one or more incremental oral devices to overcome a user's gag reflex. In aspects wherein the therapeutic oral device may be formed from a mold, the mouth guard portion and the hard palate portion may be customized to fit to the dimensions of the mouth of an intended user.

The present disclosure relates to a therapeutic oral appliance that may include a mouth guard portion, wherein the mouth guard portion may be configured to at least partially interface with one or more teeth of a user; a hard palate portion configured to at least partially interface with a hard palate of a mouth of the user, wherein the hard palate portion may extend upwardly from the mouth guard portion; a tongue retainer portion, wherein the tongue retainer portion may extend from the hard palate portion into at least a portion of a throat of the user, wherein the tongue retainer portion may comprise an upper surface, a lower surface, and a longitudinal length; and at least one airway, wherein the at least one airway may comprise one or more recesses within at least one of the upper surface of the tongue retainer portion and the lower surface of the tongue retainer portion, wherein the at least one airway may extend along at least a portion of the longitudinal length of the tongue retainer portion.

In some embodiments, the mouth guard portion may comprise at least one safety mechanism. In some implementations, the tongue retainer portion may be fixed to a distal end of the hard palate portion. In some aspects, the longitudinal length of the tongue retainer portion may be adjustable. In some embodiments, the mouth guard portion may comprise at least one external attachment configured to interface with at least one supplemental device. In some implementations, the at least one external attachment may comprise at least one aperture.

In some aspects, the at least one supplemental device may comprise a tube. In some embodiments, the mouth guard portion may comprise a universal fit that may be used by a generic user. In some implementations, the therapeutic oral appliance may be configured to interface with at least one wearable device. In some aspects, the at least one wearable device may comprise a smart watch. In some embodiments, the mouth guard portion may be configured to interface with one or more dental fixtures. In some implementations, the one or more dental fixtures may comprise braces.

In some aspects, the therapeutic oral appliance may further comprise one or more sensors or electrodes. In some embodiments, the one or more sensors or electrodes may comprise at least one of: one or more electromyography electrodes, one or more acceleromyography sensors, one or more piezoelectric myography sensors, one or more temperature sensors, one or more peripheral artery tonometry sensors, one or more photoplethysmography sensors, one or more pulse oximetry sensors, one or more moisture sensors, one or more potential hydrogen (pH) sensors, one or more audio sensors, one or more force sensors or force transducers, one or more light-emitting sensors, one or more light absorption sensors, one or more muscle movement sensors, one or more accelerometers, one or more heart rate monitors, or one or more capnography sensors.

In some implementations, the therapeutic oral appliance of the present disclosure may be configured to interface with at least one external device. In some aspects, the at least one external device may comprise at one of: a smartphone, a desktop computing device, a laptop computing device, a tablet computing device, and a medical apparatus. In some embodiments, the mouth guard portion may comprise at least one wire. In some implementations, the mouth guard portion may comprise an at least partially customized fit for a specific user. In some aspects, the mouth guard portion may be adjustable. In some embodiments, the hard palate portion may extend upwardly from the mouth guard portion to a point of central convergence.

BRIEF DESCRIPTION OF THE DRAWINGS

The accompanying drawings that are incorporated in and constitute a part of this specification illustrate several embodiments of the disclosure and, together with the description, serve to explain the principles of the disclosure:

FIG. 6A illustrates an exemplary therapeutic oral appliance comprising a tongue retainer portion, according to some embodiments of the present disclosure.

FIG. 6B illustrates an exemplary a cross-sectional view of an oral cavity with an exemplary therapeutic oral appliance, according to some embodiments of the present disclosure.

FIG. 7A illustrates an exemplary therapeutic oral appliance comprising a tongue retainer portion, according to some embodiments of the present disclosure.

FIG. 7B illustrates an exemplary cross-sectional view of an oral cavity with an exemplary therapeutic oral appliance, according to some embodiments of the present disclosure.

DETAILED DESCRIPTION

In the following sections, detailed descriptions of examples and methods of the disclosure will be given. The descriptions of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Therapeutic oral appliance: as used herein refers to a device that may be removably inserted into the mouth of a user, wherein the therapeutic oral appliance may be configured to assess one or more health aspects of the user or alleviate one or more medical conditions experienced by the user. By way of example and not limitation, a therapeutic oral appliance may at least partially alleviate sleep apnea or teeth grinding of a user or a therapeutic oral appliance may detect a body temperature or blood oxygen level of a user.

Tongue retainer portion: as used herein refers to a portion of a therapeutic oral appliance that limits backward movement of the tongue when the therapeutic oral appliance is worn. In some embodiments, a tongue retainer portion may comprise one or more airways that may prevent occlusion of the throat, allowing for unobstructed breathing.

Hard palate portion: as used herein refers to a portion of a therapeutic oral appliance that is configured to at least partially interface with the hard palate within the mouth of a user.

Mouth guard portion: as used herein refers to a portion of a therapeutic oral appliance that fits to or over at least a portion of one or more teeth of a user. In some aspects, a mouth guard portion may be customized to fit a user's teeth, such as, for example and not limitation, by using a dental mold. In some implementations, a mouth guard portion may comprise an at least partially customized fit for a specific user. In some embodiments, a mouth guard portion may comprise a substantially universal fit that may be used by any generic user without requiring a custom fitting.

OSA: as used herein refers to obstructive sleep apnea.

Figure 1A:
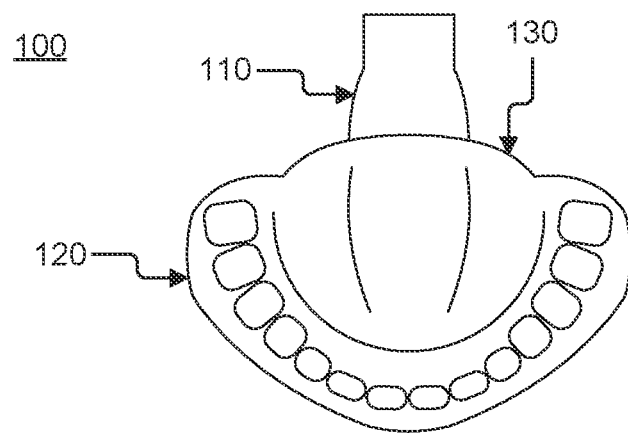
FIG. 1A illustrates a top-down view of an exemplary therapeutic oral appliance, according to some embodiments of the present disclosure.
Figure 1B:
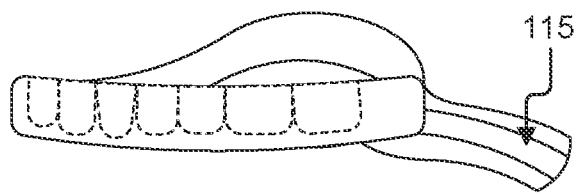
FIG. 1B illustrates a side view of an exemplary therapeutic oral appliance, according to some embodiments of the present disclosure.
Figure 1C:
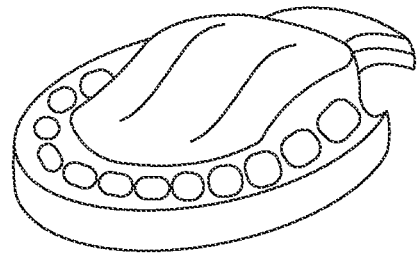
FIG. 1C illustrates a perspective view of an exemplary therapeutic oral appliance, according to some embodiments of the present disclosure.

Referring now to FIGS. 1A-1C, an exemplary therapeutic oral appliance 100 is illustrated. In some embodiments, the therapeutic oral appliance 100 may comprise a tongue retainer portion 110. In some implementations, the tongue retainer portion 110 may comprise one or more predetermined lengths. This may allow the user to gradually become accustomed to the presence of the tongue retainer portion 110 within at least a portion of the throat. Gradual introduction may allow for the suppression of the gag reflex, which may occur as the length of the tongue retainer portion 110 enters the throat. In some aspects, the tongue retainer portion 110 may comprise an upper surface, a lower surface, and a longitudinal length.

In some embodiments, the therapeutic oral appliance 100 may be utilized to relieve airway obstruction from a one or more sources. As an illustrative example, the therapeutic oral appliance 100 may directly relieve obstruction caused by obstruction at the back or base of the tongue, uvula, and soft palate. The therapeutic oral appliance 100 may partially relieve obstruction that is caused by issues below the epiglottis such as hypopharyngeal issues, vocal cord folds and arytenoids, anterior-posterior soft palate collapse, lateral soft palate collapse, complete concentric collapse, epiglottic and tonsillar collapse. The therapeutic oral appliance 100 may address a plurality of issues of obstruction simultaneously through prescribed therapeutic use.

In some implementations, the therapeutic oral appliance 100 may contribute to partial relief of obstruction by improving overall muscle tone of the oropharynx. This improvement may result as muscles resist and gain tone by resisting the therapeutic oral appliance 100. In some aspects, an airway 115 may provide airflow from the mouth to the soft palate. This may improve breathing and decrease airway obstruction.

In some embodiments, the material of the therapeutic oral appliance 100 may comprise materials that are sufficiently durable and chemical resistant to sanitize the therapeutic oral appliance 100 on a daily basis by chemical (e.g., mouth wash or alcohols) means or physical means (e.g., steam sterilization), as non-limiting examples. In some implementations, the removable aspect of the therapeutic oral appliance 100 may allow the user to clean and sanitize the therapeutic oral appliance 100 frequently. This may facilitate accessible cleaning that may reduce the possibility of tissue necrosis and infection, as a non-limiting list.

In some implementations, the therapeutic oral appliance 100 may comprise a hard palate portion 130. In some embodiments, the mating connected by symmetric surfaces between the hard palate and the hard palate portion 130 may improve the stability of the therapeutic oral appliance 100 within the oral cavity. In some aspects, the therapeutic oral appliance 100 may comprise a mouth guard portion 120. In some additional aspects, the hard palate portion 130 may extend upward from the mouth guard portion 120 to a central point of convergence.

In some embodiments, the mouth guard portion 120 may comprise a composite of materials. This may prevent fracture and fragment wear that could cause worn parts of the therapeutic oral appliance 100 to be swallowed. In some implementations, the substrate material may be embedded within the primary material.

As an example, a hard plastic plate may be embedded in the medium of ethylene-vinyl acetate (EVA), or an elastomeric polymer, as the softer plastic cures within the teeth mold. In some aspects, the embedded substrate may be fragmentary. As another example, an EVA material may have plates of harder plastic embedded in the regions over the rear molars to reduce wear from teeth grinding. In some embodiments, the therapeutic oral appliance 100 may comprise a coated aspect. As an example, the therapeutic oral appliance 100 may be coated in a hardened plastic film that reduces torsional fatigue within the structure of the therapeutic oral appliance 100.

The mouth guard portion 120 may be configured to at least partially interface with one or more teeth of a user. This interface may maintain the position of the therapeutic oral appliance 100 in the mouth and prevent ingestion of the therapeutic oral appliance 100. In some aspects, the therapeutic oral appliance 100 may comprise a hard palate portion 130. The hard palate portion 130 may interface with the hard palate within the mouth. In some implementations, the mouth guard portion 120 and the hard palate portion 130 may reduce point pressure by spreading the retaining force for the therapeutic oral appliance 100 across a larger surface area.

The mouth guard portion 120 may provide protection to the soft sensitive tissue of the oral pharynx. A mouth guard portion 120 may protect the parts of the hard palate, soft palate, and oral pharynx from pressure points, as a non-limiting list. The pressure may originate from the oral airway. The mouth guard portion 120 may prevent pain and possible tissue necrosis by preventing these pressure points. In some aspects, the mouth guard portion 120 may extend to cover the hard and soft palate to protect sensitive tissues. This protection may assist in pushing the oral airway away from the oropharynx. In some embodiments, moving the oral airway away from the oropharynx may decrease the gag reflex.

In some implementations, the level of customization of the therapeutic oral appliance 100 may vary. As an illustrative example, a user may receive a dental impression in a dentist's office that provides a high-fidelity model of the unique aspects of the user's mouth. This impression may be formed via physical or digital dental impression. This impression may become the casting for the therapeutic oral appliance 100. This high level of customization may allow the fit of the therapeutic oral appliance 100 to match the form of the hard palate and teeth with precision. It may also improve the overall comfort and performance of the oral device. The oral device can be customized to fit each user's unique dentition, maxillary or dental arch, palatal arch or vault, and palatal mucosa and algae, thus making the least intrusive oral airway size and path for maximal comfort.

As another illustrative example, a user may purchase a therapeutic oral appliance 100 remotely. The therapeutic oral appliance 100 may be delivered as a generic casting of a therapeutic oral appliance 100. The generic mold may fit most mouths in a loose composition. The generic casting may then become pliable after boiling it in water. This pliability may allow the user to press the therapeutic oral appliance 100 firmly into their mouth to allow the therapeutic oral appliance 100 to harden in the shape of the user's mouth. This formed fit may provide sufficient stability, without requiring a dentist visit.

In some embodiments, the therapeutic oral appliance 100 may interface with the oral cavity. The quality of the interface may contribute to safety, comfort, and effectiveness as a therapeutic device, as a non-limiting list. In some implementations, the removable aspect of the therapeutic oral appliance 100 may also provide opportunity for frequent sanitation. This may prevent infection, inflammation, and tissue necrosis, as non-limiting examples.

In some embodiments, the mouth guard portion 120 may interface with the teeth. This interface may maintain the position of the therapeutic oral appliance 100 in the mouth and prevent ingestion of the therapeutic oral appliance 100. In some aspects, the therapeutic oral appliance 100 may comprise a hard palate portion 130. The mouth guard portion 120 and the hard palate portion 130 may reduce the probability of subconscious rejection of the therapeutic oral appliance 100 by spitting it out. The custom fit of the therapeutic oral appliance 100 may reduce this probability by increasing comfort. In some aspects, the interface between the therapeutic oral appliance 100 and the oral cavity may assist in alignment of the tongue retainer portion 110 within the throat. Unsecured movement of the tongue retainer portion 110 may result in triggering the gag reflex or choking.

In some embodiments, the tongue retainer portion 110 may be fixed to and extend from a distal end of the hard palate portion 130 into at least a portion of the throat sufficient to reduce movement of the tongue. In some implementations, the tongue retainer portion 110 may be trimmable for preferential comfort and fit within the throat, as non-limiting examples. In some aspects, the tongue retainer portion 110 may prevent the tongue from falling back and touching the soft palate, which may otherwise create airway obstruction. In some embodiments, the tongue retainer portion 110 may comprise an airway 115 that ensures airflow when the tongue retainer portion 110 occupies the throat.

In some aspects, the tongue retainer portion 110 may comprise an airway 115. In some implementations, the airway 115 may comprise one or more recesses or slots within the upper and/or lower surface of the tongue retainer portion 110 that extend along at least a portion of the longitudinal length of the tongue retainer portion 110, thereby forming one or more channels or grooves. In some embodiments, airway 115 channels may provide an airway to allow air flow. In some implementations, the airway 115 may follow the natural anatomical airway passage of the user. This may decrease the chance of inadvertent airway obstruction by the therapeutic oral appliance 100. The conformity to the natural anatomy of the oral cavity may result from the custom fit of the therapeutic oral appliance 100.

Figure 2A:
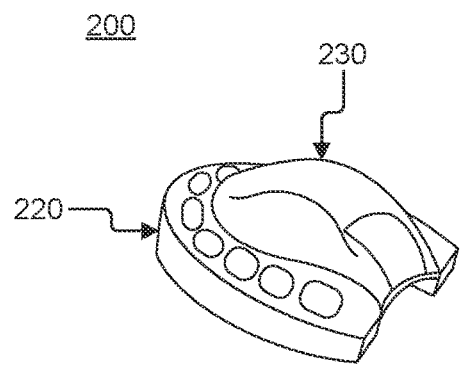
FIG. 2A illustrates an exemplary therapeutic oral appliance, according to some embodiments of the present disclosure.
Figure 2B:
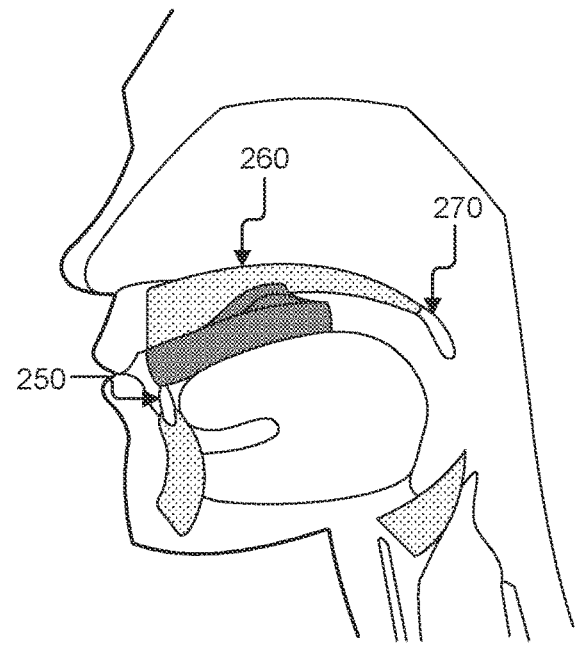
FIG. 2B illustrates a cross-sectional view of an oral cavity with an exemplary therapeutic oral appliance, according to some embodiments of the present disclosure.

Referring now to FIG. 2A, an exemplary therapeutic oral appliance 200 is illustrated. Referring now to FIG. 2B, a cross-sectional view of an oral cavity with an exemplary therapeutic oral appliance 200 is illustrated. In some embodiments, the therapeutic oral appliance 200 may comprise a hard palate portion 230. In some implementations, the therapeutic oral appliance 200 may comprise a mouth guard portion 220. In some aspects, the hard palate portion 230 may extend upward from the mouth guard portion 220 to a central point of convergence.

In some embodiments, the hard palate portion 230 may interface with the hard palate 260. In some aspects, the surface of the hard palate portion 230 may mirror the geometry of the hard palate 260 to provide a custom fit. In some embodiments, the hard palate portion 230 may comprise identical geometry to the hard palate 260 by being cured in a mold formed from an impression of the user's oral cavity. In some implementations, this mold may be a standard mold used in creating denture impressions.

In some implementations, the distal end of the therapeutic oral appliance 200 may align with the beginning of the soft palate 270 within the oral cavity. This may prevent damage from continual applied force on the soft palate 270. In some implementations, the mouth guard portion 220 may interface with the teeth 250. In some aspects, the interaction between the guard portion 220 and the teeth 250 may operate as a mated interface that is formed by curing the resin for the therapeutic oral appliance 200 within a casting made from an impression of the user's teeth 250.

A patient may wear a therapeutic oral appliance 200 without tongue retainer portion to begin the incremental process to suppress the gag reflex. Wearing a therapeutic oral appliance 200 may be uncomfortable at first, particularly for those who are unaccustomed to wearing oral appliances. A patient may get used to the therapeutic oral appliance 200 by wearing it for a few hours and then overnight, as a way to build up to the gag reflex suppression process with the tongue retainer portion.

In some embodiments, the mouth guard portion 220 may comprise a generic cast that, upon inducing heat to increase malleability, may be formed to the shape of the intended teeth 250. This may provide greater comfort when wearing the therapeutic oral appliance 200. A formed therapeutic oral appliance 200 may prevent unconscious reject from the mouth. For example, a user may unconsciously spit out the therapeutic oral appliance while sleeping unless the therapeutic oral appliance 200 is homogeneous with the structure of the oral cavity.

In some aspects, the mouth guard portion 220 may comprise a cavity designed to enclose a plurality of teeth 250 simultaneously. The thickness of the outside edge of the mouth guard portion 220 may be of minimal thickness to ensure an unobstructive fit within the oral cavity. In some embodiments, a minimal thickness may increase the comfort of the therapeutic oral appliance 200 and the effectiveness of therapeutic utilization by avoiding subconscious rejection, as non-limiting examples.

Figure 3A:
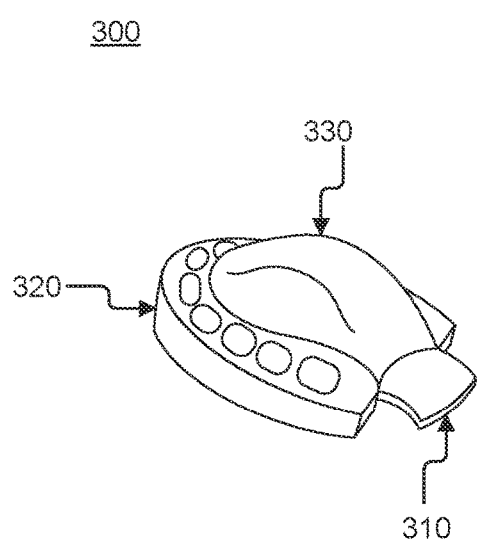
FIG. 3A illustrates an exemplary therapeutic oral appliance comprising a tongue retainer portion, according to some embodiments of the present disclosure.
Figure 3B:
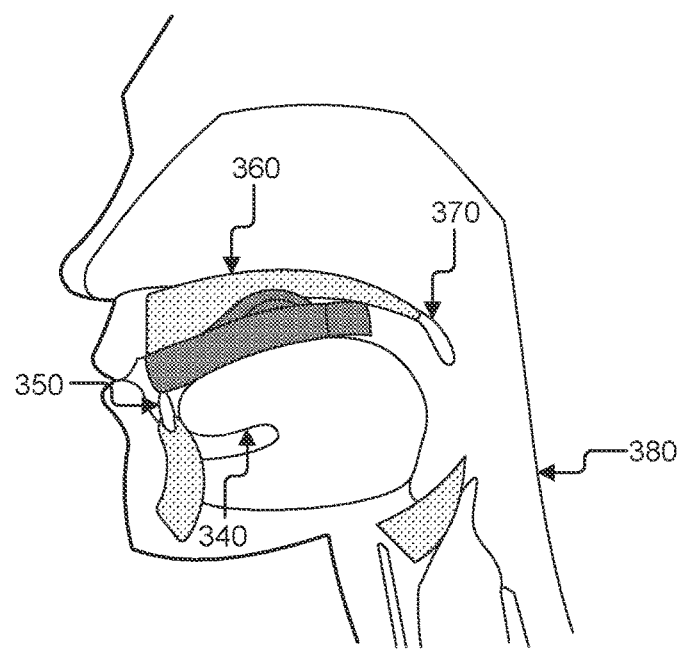
FIG. 3B illustrates an exemplary cross-sectional view of an oral cavity with an exemplary therapeutic oral appliance, according to some embodiments of the present disclosure.

Referring now to FIG. 3A, an exemplary therapeutic oral appliance 300 comprising a tongue retainer portion 310 is illustrated. Referring now to FIG. 3B, an exemplary a cross-sectional view of an oral cavity with an exemplary therapeutic oral appliance 300 is illustrated. In some embodiments, the therapeutic oral appliance 300 may comprise a hard palate portion 330. In some implementations, the therapeutic oral appliance 300 may comprise a mouth guard portion 320. In some embodiments, the hard palate portion 330 may interface with the hard palate 360.

In some implementations, the tongue retainer portion 310 may align with the soft palate 370. In some embodiments, the tongue retainer portion 310 may comprise an upper surface, a lower surface, and a longitudinal length. In some aspects, the therapeutic oral appliance 300 may enter the throat 380 via the tongue retainer portion 310. In some implementations, the therapeutic oral appliance 300 may comprise a tongue retainer portion 310 of a plurality of predetermined lengths. This may allow the user to gradually become accustomed to the presence of the tongue retainer portion 310 within the throat 380. This may train the gag reflex to refrain from engaging the tongue retainer portion 310 sufficient to allow the user to insert the therapeutic oral appliance 300 daily. In some embodiments, the tongue retainer portion 310 may be fixed to a distal end of the hard palate portion 330.

In some embodiments, the therapeutic oral appliance 300 may interface with the tongue 340. In some aspects, the tongue retainer portion 310 may direct the tongue 340 through the physical presence of the tongue retainer portion 310. In some embodiments, the tongue retainer portion 310 may restrain the tongue 340 sufficient to facilitate unobstructed breathing.

For example, a person in a coma may need a clear airway to receive sufficient oxygen. In an unconscious state, the tongue 340 may otherwise reduce or impair the user's airway. In some implementations, the mouth guard portion 320 may be configured to at least partially interface with one or more teeth 350. This may prevent the therapeutic oral appliance 300 from dislodgement and potential ingestion.

Figure 4A:
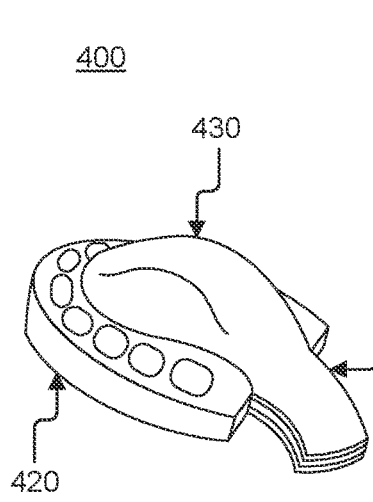
FIG. 4A illustrates an exemplary therapeutic oral appliance comprising a tongue retainer portion, according to some embodiments of the present disclosure.
Figure 4B:
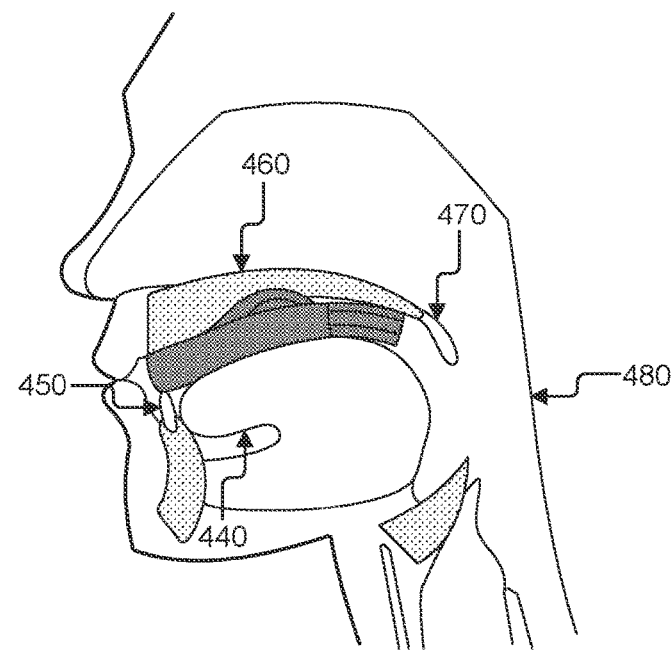
FIG. 4B illustrates an exemplary a cross-sectional view of an oral cavity with an exemplary therapeutic oral appliance, according to some embodiments of the present disclosure.

Referring now to FIG. 4A, an exemplary therapeutic oral appliance 400 comprising a tongue retainer portion 410 is illustrated. Referring now to FIG. 4B, an exemplary a cross-sectional view of an oral cavity with an exemplary therapeutic oral appliance 400 is illustrated. In some embodiments, the therapeutic oral appliance 400 may comprise a hard palate portion 430. In some implementations, the therapeutic oral appliance 400 may comprise a mouth guard portion 420. In some aspects, the hard palate portion 430 may extend upward from the mouth guard portion 420 to a central point of convergence.

In some embodiments, the hard palate portion 430 may interface with the hard palate 460. In some implementations, the tongue retainer portion 410 may align with the soft palate 470. In some embodiments, the tongue retainer portion 410 may comprise an upper surface, a lower surface, and a longitudinal length. In some aspects, the therapeutic oral appliance 400 may enter the throat 480. In some implementations, the tongue retainer portion 410 may enter the throat incrementally to avoid triggering a gag reflex. In some embodiments, the tongue retainer portion 410 may be fixed to a distal end of the hard palate portion 430.

A gag reflex is a contraction of the throat that occurs when an object makes contact with the back of the tongue 440 or throat 480. This gag reflex may be overcome through incremental introduction of the tongue retainer portion 410 into the throat 480. In some aspects, this may be introduced by wearing a therapeutic oral appliance 400 with an incremental increase in tongue retainer portion length 410 for a predetermined time.

The length of the tongue retainer portion 410 may be sufficiently short to prevent the grasping of the tongue retainer portion 410 by the throat 480 via throat contraction caused by the gag reflex. The length of the tongue retainer portion 410 may be sufficiently short to prevent irregular swallowing due to the throat exerting a downward force on the therapeutic oral appliance 400 by grasping the end of the tongue retainer portion 410 during throat contraction.

In some embodiments, the therapeutic oral appliance 400 may interface with the tongue 440. In some embodiments, the tongue retainer portion 410 may restrain the tongue 440 sufficiently to facilitate unobstructed breathing. In some implementations, the mouth guard portion 420 may be configured to at least partially interface with one or more teeth 450. In some aspects, the mouth guard portion 420 may secure the therapeutic oral appliance 400 within the oral cavity. This may prevent ingestion of the therapeutic oral appliance 400.

Figure 5A:
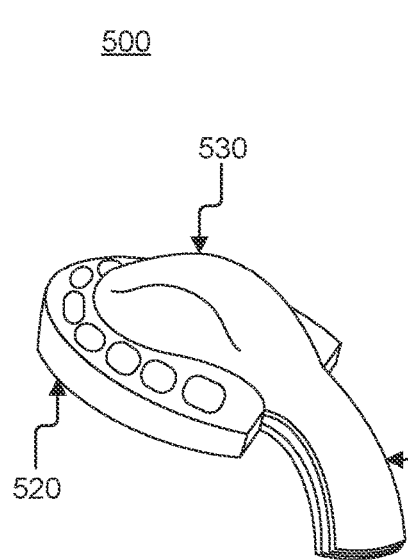
FIG. 5A illustrates an exemplary therapeutic oral appliance comprising a tongue retainer portion, according to some embodiments of the present disclosure.
Figure 5B:
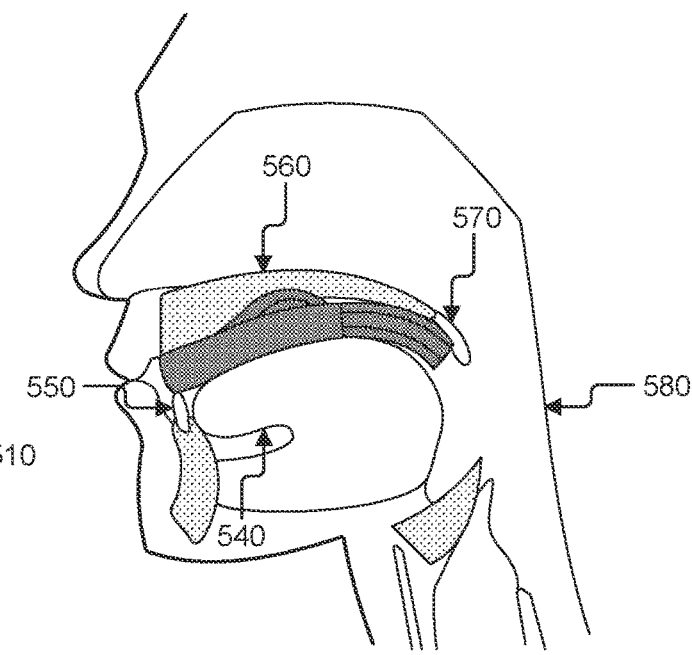
FIG. 5B illustrates an exemplary a cross-sectional view of an oral cavity with an exemplary therapeutic oral appliance, according to some embodiments of the present disclosure.

Referring now to FIG. 5A, an exemplary therapeutic oral appliance 500 comprising a tongue retainer portion 510 is illustrated. Referring now to FIG. 5B, an exemplary a cross-sectional view of an oral cavity with an exemplary therapeutic oral appliance 500 is illustrated. In some embodiments, the therapeutic oral appliance 500 may comprise a hard palate portion 530. In some embodiments, the hard palate portion 530 may interface with the hard palate 560. The interface between the hard palate 560 and the hard palate portion 530 may provide stability that reduces movement of the tongue retainer portion 510 within the throat 580.

In some implementations, the therapeutic oral appliance 500 may comprise a mouth guard portion 520. In some implementations, the hard palate portion 530 may extend upward from the mouth guard portion 520 to a central point of convergence. In some implementations, the mouth guard portion 520 may be configured to at least partially interface with one or more teeth 550. In some aspects, the mouth guard portion 520 may provide a generic fit to the teeth 550 with limited malleable properties. This generic tooth form may provide sufficient stability to prevent ingestion of the therapeutic oral appliance 500.

In some implementations, the tongue retainer portion 510 may align with the soft palate 570. In some embodiments, the tongue retainer portion 510 may comprise an upper surface, a lower surface, and a longitudinal length. In some aspects, the therapeutic oral appliance 500 may enter the throat 580. In some implementations, the user may modify the length of the tongue retainer portion 510. In some aspects, the tongue retainer portion 510 may be shortened by severing the tongue retainer portion 510 with scissors to the desired length. This may allow a user to customize the length of the tongue retainer portion 510. Shortening the tongue retainer portion 510 may be necessary if the tongue retainer portion 510 extends into the throat 580 sufficient to trigger the gag reflex. In some embodiments, the therapeutic oral appliance 500 may interface with the tongue 540.

Referring now to FIG. 6A, an exemplary therapeutic oral appliance 600 comprising a tongue retainer portion 610 is illustrated. Referring now to FIG. 6B, an exemplary a cross-sectional view of an oral cavity with an exemplary therapeutic oral appliance 600 is illustrated. In some embodiments, the therapeutic oral appliance 600 may comprise a hard palate portion 630. In some implementations, the therapeutic oral appliance 600 may comprise a mouth guard portion 620. In some aspects, the hard palate portion 630 may extend upward from the mouth guard portion 620 to a central point of convergence. In some implementations, the mouth guard portion 620 may be configured to at least partially interface with one or more teeth 650.

In some embodiments, the hard palate portion 630 may interface with the hard palate 660. In some implementations, the tongue retainer portion 610 may align with the soft palate 670. In some embodiments, the tongue retainer portion 610 may comprise an upper surface, a lower surface, and a longitudinal length. In some aspects, the tongue retainer portion 610 may be fixed to a distal end of the hard palate portion 630 and encroach into the throat 680. In some implementations, the tongue retainer portion 610 may increase in length incrementally.

As an illustrative example, a user may, upon ordering the therapeutic oral appliance, receive a plurality of therapeutic oral appliances comprising therapeutic oral appliances with incremental tongue retainer portions, such as described in FIGS. 2A-6A. In preparation for using the therapeutic capabilities of the therapeutic oral appliance, the user may use a therapeutic oral appliance with incrementally longer tongue retainer portions until snoring is effectively prevented. A user may wear each size for a few days to a few weeks each, depending on the comfort level of each therapeutic oral appliance. The user may use the therapeutic oral appliance daily while sleeping to acclimate the throat to the tongue retainer portion and overcome the gag reflex.

Dependent upon individual anatomy, the user may discover that an intermediary length of the tongue retainer portion is of sufficient length for therapeutic purposes, where the user may not benefit from an incrementally longer tongue retainer portion. In some embodiments, the user may incrementally increase the length of the tongue retainer portion 610 until the length is sufficient to relieve obstruction but remain sufficiently comfortable for use while sleeping. In some aspects, the user may discover a need to trim the length of the tongue retainer portion 610 of the therapeutic oral appliance to achieve a desired length that is between the incremental tongue retainer portions. In some implementations, the length of the tongue retainer portion 610 may remain shorter than the distance to the epiglottis to ensure swallowing remains possible.

Referring now to FIG. 7A, an exemplary therapeutic oral appliance 700 comprising a tongue retainer portion 710 is illustrated, wherein the therapeutic oral appliance 700 is fitted for a child. Referring now to FIG. 7B, an exemplary a cross-sectional view of an oral cavity with an exemplary therapeutic oral appliance 700 is illustrated. In some embodiments, the therapeutic oral appliance 700 may comprise a hard palate portion 730. In some implementations, the therapeutic oral appliance 700 may comprise a mouth guard portion 720. In some aspects, the hard palate portion 730 may extend upward from the mouth guard portion 720 to a central point of convergence.

In some embodiments, the hard palate portion 730 may interface with the hard palate 760. In some implementations, the tongue retainer portion 710 may align with the soft palate 770. In some embodiments, the tongue retainer portion 710 may comprise an upper surface, a lower surface, and a longitudinal length. In some aspects, the therapeutic oral appliance 700 may enter the throat 780. In some embodiments, the therapeutic oral appliance 700 may interface with the tongue 740. In some implementations, the mouth guard portion 720 may be configured to at least partially interface with one or more teeth 750.

For smaller mouths, such as with children, incremental increases in tongue retainer portions 710 may be smaller to allow for a more refined fit. Smaller size increases may allow for easier transition with increased likelihood that the gag reflex suppression may occur without issue. Smaller mouths may require shorter tongue retainer portions 710. In some aspects, the incremental sizes of tongue retainer portions 710 may depend on predefined factors, such as strength of gag reflex, mouth size, user preference, practitioner recommendations, or level of customization. For example, where the therapeutic oral appliance is prescribed by a practitioner, the increments may be more customized than an over-the-counter version of a therapeutic oral appliance.

Figure 8A:
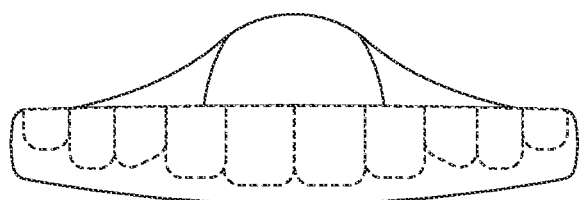
FIG. 8A illustrates a front view of an exemplary therapeutic oral appliance, according to some embodiments of the present disclosure.
Figure 8B:
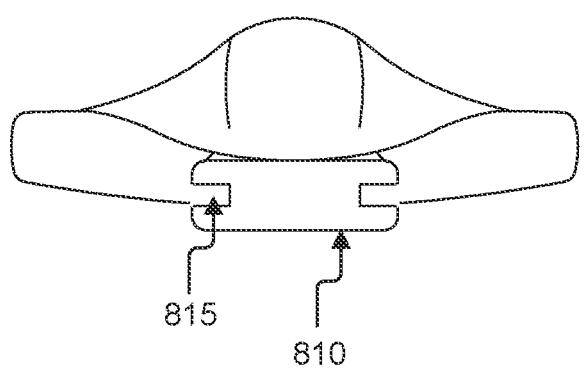
FIG. 8B illustrates a rear view of an exemplary therapeutic oral appliance, according to some embodiments of the present disclosure.

Referring now to FIGS. 8A-8B, a front view of an exemplary therapeutic oral appliance 800 is illustrated. In some embodiments, the tongue retainer portion 810 of the therapeutic oral appliance 800 may comprise one or more uniform recesses or slots that span the longitudinal length of the tongue retainer portion 810 to create an airway 815. In some implementations, the airway 815 may comprise uniform indentations along the sidewall of the tongue retainer portion 810. In some aspects, the airway 815 may comprise air flow pathways that are parallel to the direction of the throat.

For example, the tongue retainer portion 810 may comprise one or more airway 815 tubes that continue for the longitudinal length of the tongue retainer portion 810. This may be useful if the throat is inflamed or otherwise restricted so as to render embedded channels within the walls of the tongue retainer portion 810 ineffective. In some embodiments, the airway 815 may comprise an integrated tube that runs through the center of the tongue retainer portion 810. This may reduce the required insertion diameter and prevent obstruction by utilizing existing material that extends the length of the therapeutic oral appliance 800.

Figure 9:
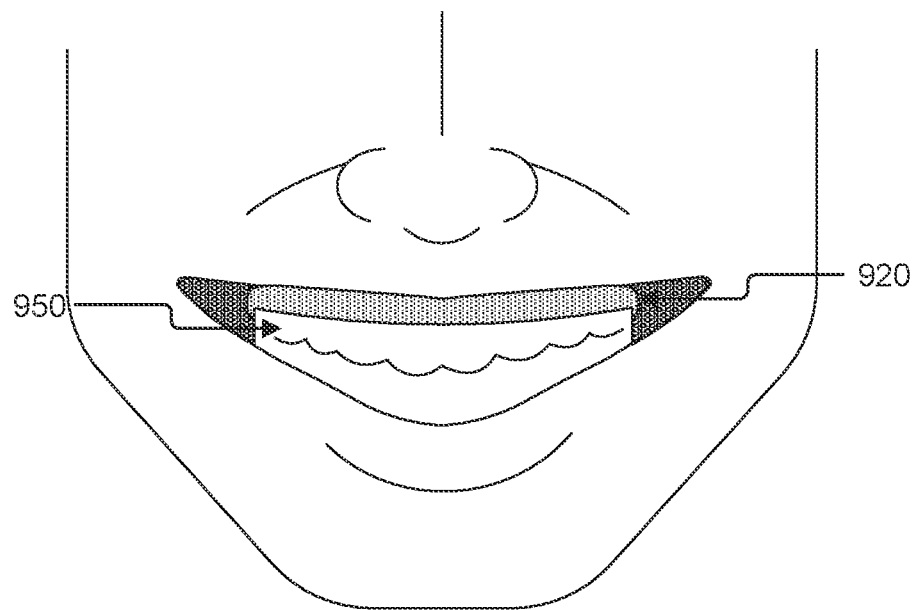
FIG. 9 illustrates a mouth wearing an exemplary therapeutic oral appliance, according to some embodiments of the present disclosure.

Referring now to FIG. 9, a mouth wearing an exemplary therapeutic oral appliance 900 is illustrated. In some embodiments, the mouth guard portion 920 may be configured to at least partially interface with one or more teeth 950 in a form fit. The therapeutic oral appliance 900 may fit similarly to a sport mouth guard, teeth whitening tray, incremental braces systems, or teeth grinding protectors, as non-limiting examples. In some aspects, a therapeutic oral appliance 900 may fit over dentures. In some embodiments, a therapeutic oral appliance 900 may fit over gums for user's who may remove their dentures at night.

Figure 10:
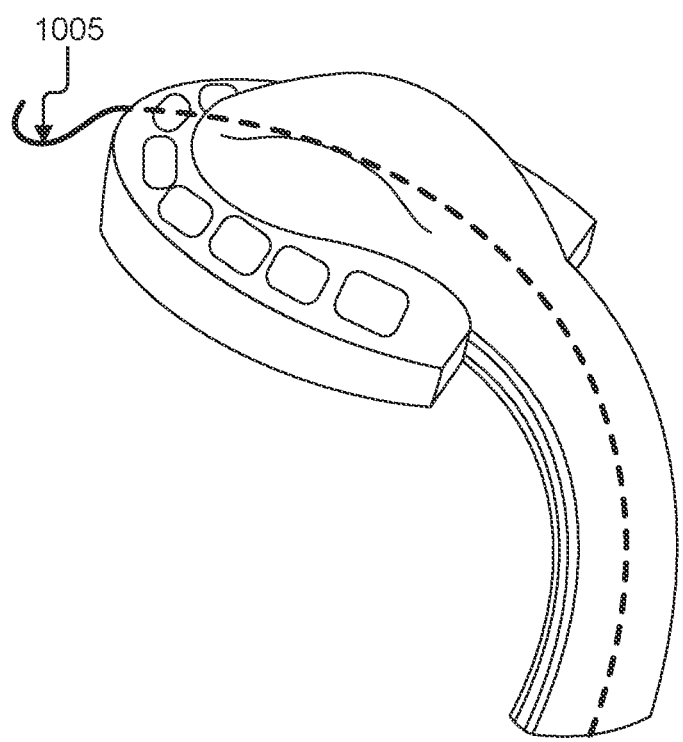
FIG. 10 illustrates an exemplary therapeutic oral appliance with a safety mechanism, according to some embodiments of the present disclosure.

Referring now to FIG. 10, an exemplary therapeutic oral appliance 1000 with a safety mechanism is illustrated. In some embodiments, the therapeutic oral appliance 1000 may comprise at least one safety mechanism 1005. In some implementations, the safety mechanism 1005 may extend the entirety of the length of the therapeutic oral appliance 1000. In some aspects, this may prevent the ingestion of a portion of the therapeutic oral appliance 1000 that may break off from the therapeutic oral appliance 1000. This may be possible after prolonged use creates fatigue within the therapeutic oral appliance 1000 that creates structural instability within the therapeutic oral appliance 1000.

Figure 11A:
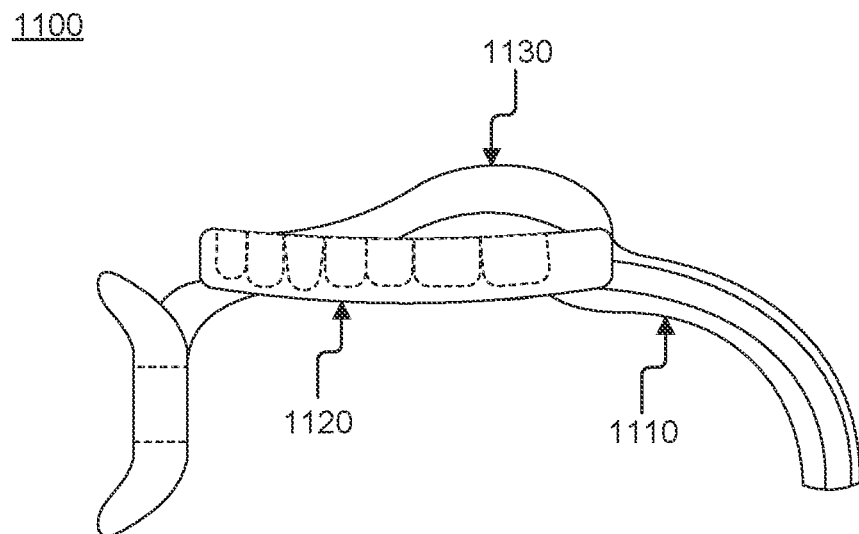
FIG. 11A illustrates a side view of an exemplary therapeutic oral appliance with a mouth guard portion attachment, according to some embodiments of the present disclosure.
Figure 11B:
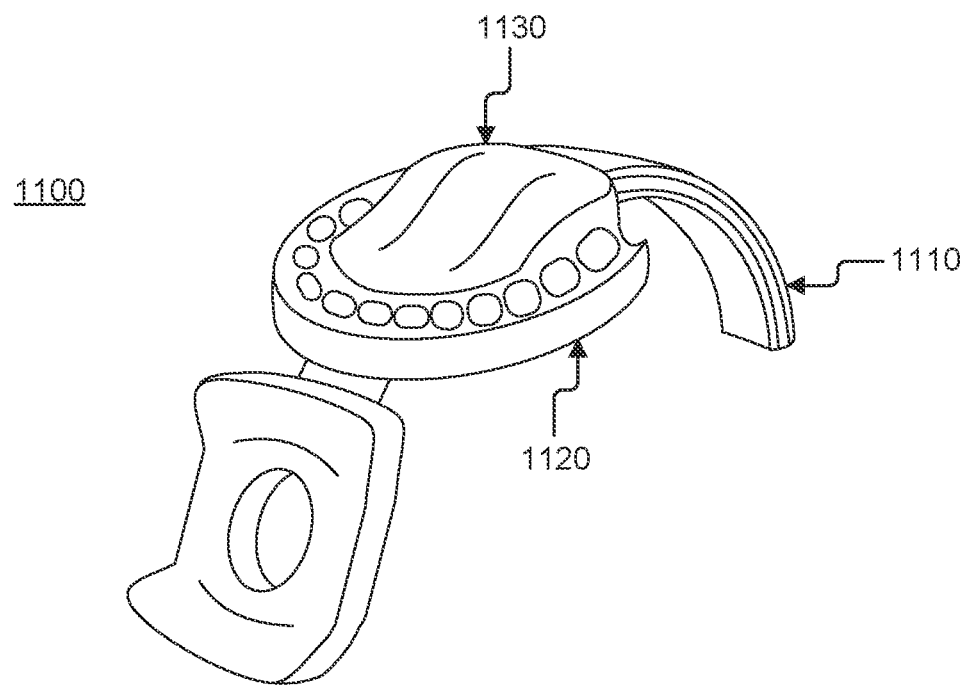
FIG. 11B illustrates a perspective view of an exemplary therapeutic oral appliance with a mouth guard portion attachment, according to some embodiments of the present disclosure.

Referring now to FIGS. 11A-11B, an exemplary therapeutic oral appliance 1100 with a mouth guard portion 1120 attachment is illustrated. In some embodiments, the mouth guard portion 1120 may comprise at least one external attachment. In some aspects, the external attachment may maintain a partially opened state for the mouth. In some implementations, the external attachment may be configured to interface with at least one supplemental device. The external attachment may comprise at least one aperture or opening that allows for the insertion of a variety of supplemental devices in the form of tubes into the oral cavity.

As an example, an anesthesiologist may insert tubes to regulate sedation during surgery. This opening in the external attachment, with support from the hard palate portion 1130, may provide stability that allows the tube to remain in a fixed state. A source of humidified air or oxygen may be diffused near the oral cavity to provide humidification. This may assist in preventing dryness in the mouth and oropharynx. The reduced dryness may provide increased user comfort. As another example, a feeding tube may interface with the external attachment to provide nutrition to a user in a coma. Supplemental tubes may also sustain health for users with a variety of health challenges.

As an illustrative example, a tube opening may provide access to the oral cavity while a user undergoes an epileptic seizure. The tongue retainer portion 1110 may assist in stabilizing the tongue and maintaining an unobstructed airway. The tube opening may assist in dampening muscular contractions within the jaw that may otherwise harm the user during the epileptic seizure. The tube opening may also maintain an orifice for the duration of the episode in case vomiting occurs.

Physical disabilities may also necessitate the utilization of supplemental tubes for sustenance. For example, a user with cerebral palsy may struggle with aspiration due to muscle weakness. This may necessitate a breathing tube. Due to other muscular atrophy and fatigue, a feeding tube may also be employed to ensure adequate nutrition. A therapeutic oral appliance 1100 may allow for prolonged use with reduced risk of damage to a user's mouth, throat, respiratory system, and overall health.

Figure 12A:
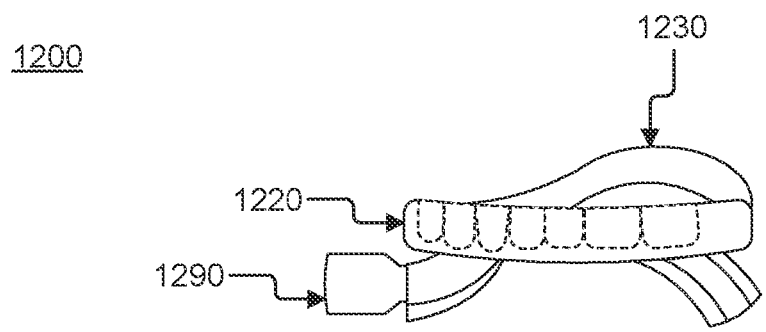
FIG. 12A illustrates a side view of an exemplary therapeutic oral appliance interfacing with an external device, according to some embodiments of the present disclosure.
Figure 12B:
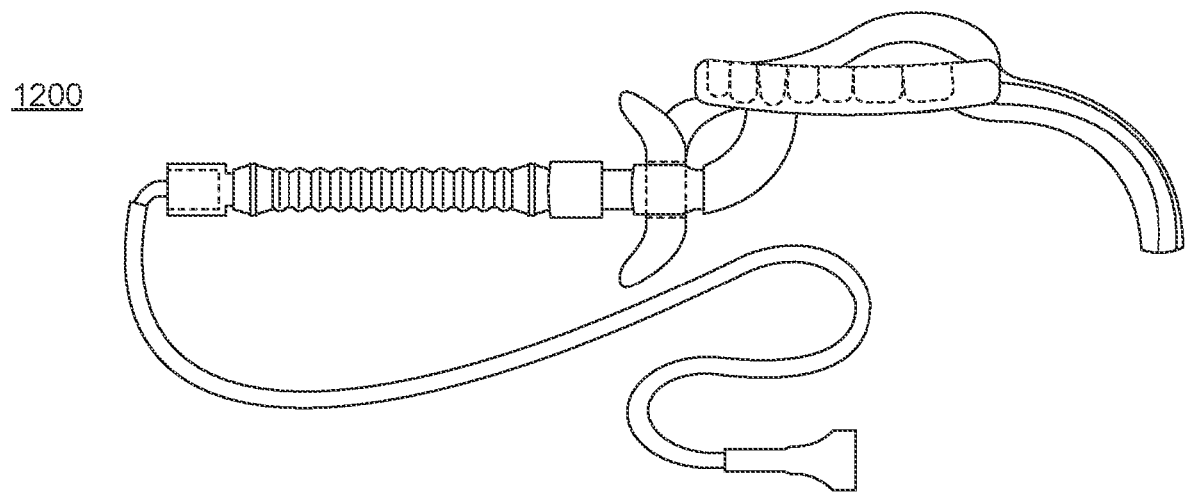
FIG. 12B illustrates a side view of an exemplary therapeutic oral appliance interfacing with an external device, according to some embodiments of the present disclosure.
Figure 12C:
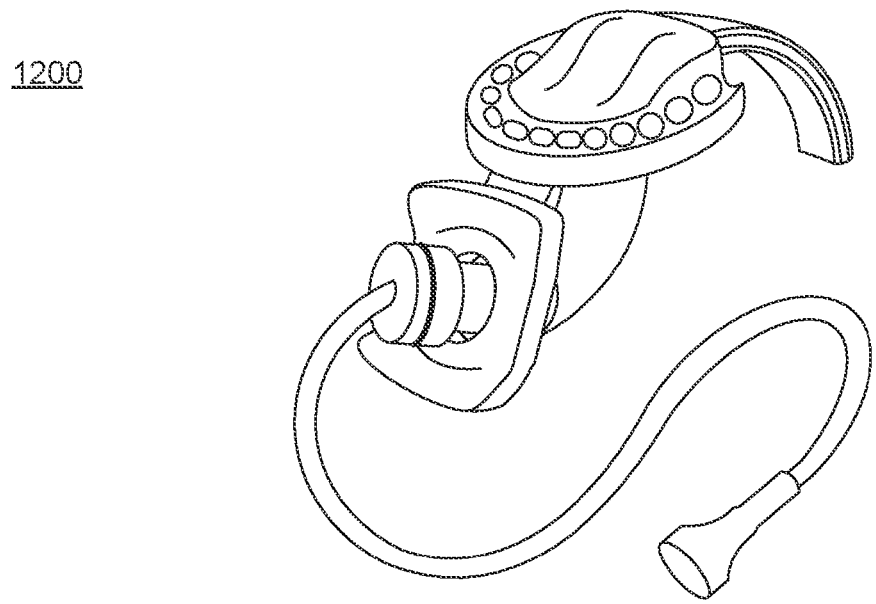
FIG. 12C illustrates a perspective view of an exemplary therapeutic oral appliance interfacing with an external device, according to some embodiments of the present disclosure.

Referring now to FIGS. 12A-12B, an exemplary therapeutic oral appliance 1200 with a mouth guard portion 1220 attachment is illustrated. In some embodiments, the mouth guard portion 1220 may comprise at least one external attachment. In some implementations, the mouth guard portion 1220 may interface with at least one supplemental device 1290. In some embodiments, the mouth guard portion 1220 may interface with at least one supplemental device 1290 via the external attachment. In some aspects, the external attachment may maintain a partially opened state for the mouth. In some embodiments, the external attachment may comprise an aperture or opening that allows for the insertion of a variety of supplemental devices 1290 in the form of tubes into the oral cavity.

As an example, an anesthesiologist may insert a tube to regulate sedation during surgery. This opening in the external attachment, with support from the hard palate portion 1230, may provide stability that allows the tube to remain in a fixed state. The opening in the external attachment may comprise a similar diameter to commonly interfaced sedation tubes. A source of humidified air or oxygen may be diffused near the oral cavity to provide humidification. This may assist in preventing dryness in the mouth and oropharynx. The reduced dryness may provide increased user comfort.

Physical disabilities may also necessitate the utilization of supplemental tubes for sustenance. For example, a user with cerebral palsy may struggle with aspiration due to muscle weakness. This may necessitate a breathing tube. Due to other muscular atrophy and fatigue, a feeding tube may also be employed to ensure adequate nutrition. A therapeutic oral appliance 1200 may allow for prolonged use with reduced risk of damage to a user's mouth, throat, respiratory system, and overall health.

Figure 13A:
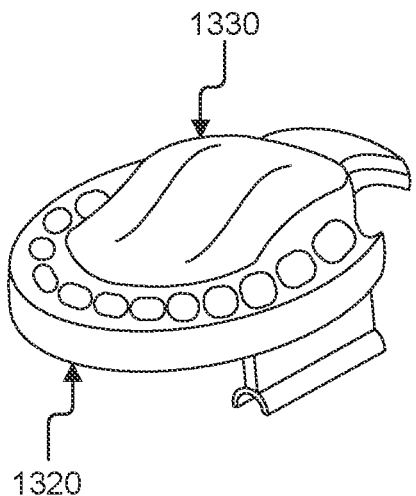
FIG. 13A illustrates a side view of an exemplary therapeutic oral appliance with a mouth guard portion attachment, according to some embodiments of the present disclosure.
Figure 13B:
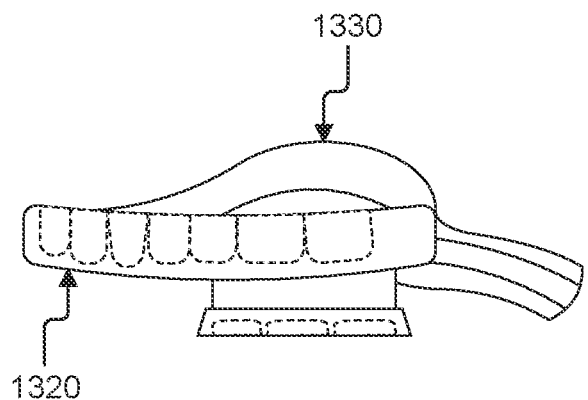
FIG. 13B illustrates a perspective view of an exemplary therapeutic oral appliance with a mouth guard portion attachment, according to some embodiments of the present disclosure.

Referring now to FIGS. 13A-13B, a side view of exemplary therapeutic oral appliance 1300 with a mouth guard portion attachment is illustrated. In some embodiments, the therapeutic oral appliance 1300 may comprise a mouth guard portion 1320. In some implementations, the mouth guard portion 1320 may comprise an attachment to prevent the grinding of the teeth. In some aspects, the therapeutic oral appliance 1300 may comprise a hard palate portion 1330 that may assist with reducing translational movement caused by teeth grinding. In some implementations, the hard palate portion 1330 may extend upward from the mouth guard portion 1320 to a central point of convergence.

Figure 14A:
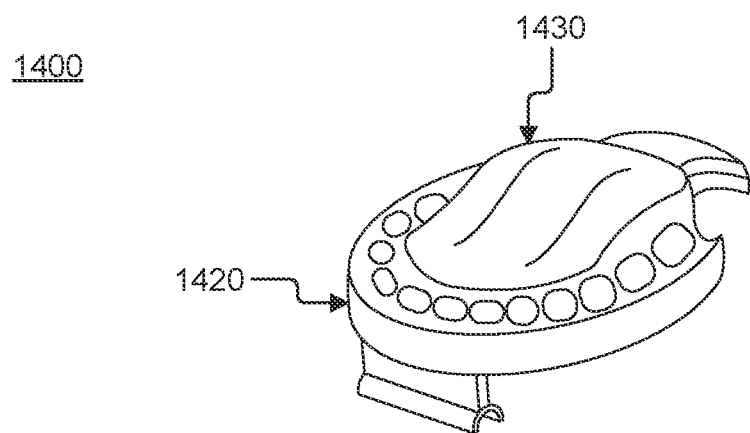
FIG. 14A illustrates a side view of an exemplary therapeutic oral appliance with a mouth guard portion attachment, according to some embodiments of the present disclosure.
Figure 14B:
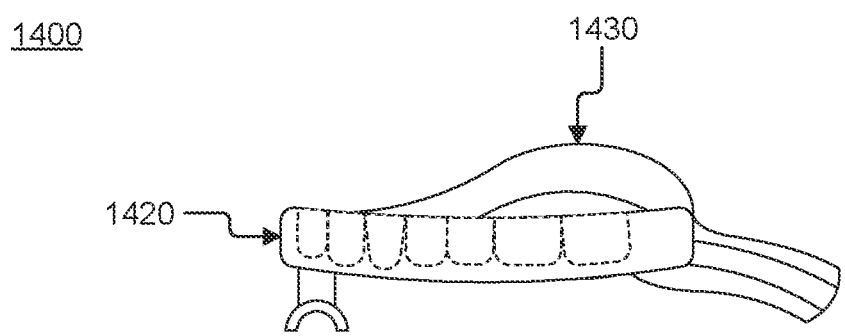
FIG. 14B illustrates a perspective view of an exemplary therapeutic oral appliance with a mouth guard portion attachment, according to some embodiments of the present disclosure.

Referring now to FIG. 14A-14B, a side view of exemplary therapeutic oral appliance 1400 with a mouth guard portion attachment is illustrated. In some embodiments, the therapeutic oral appliance 1400 may comprise a mouth guard portion 1420. In some implementations, the mouth guard portion 1420 may comprise an attachment to prevent the grinding of the teeth. In some aspects, the therapeutic oral appliance 1400 may comprise a hard palate portion 1430 that may assist with reducing translational movement caused by teeth grinding. In some embodiments, the hard palate portion 1430 may extend upward from the mouth guard portion 1420 to a central point of convergence.

In some aspects, the therapeutic oral appliance 1400 may interface with the lower jaw via attachment to a lower therapeutic oral appliance 1400. In some embodiments, a therapeutic oral appliance may cover the lower teeth. In some implementations, the therapeutic oral appliance may connect to the therapeutic oral appliance 1400 secured to the upper palate. This may increase comfort and security, as non-limiting attributes. A lower therapeutic oral appliance may decrease the probability of the user spitting out the therapeutic oral appliance 1400.

Figure 15A:
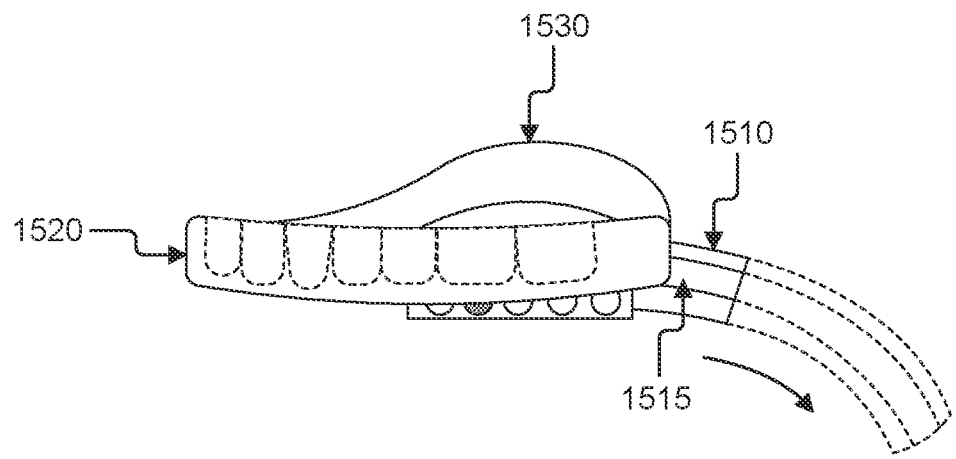
FIG. 15A illustrates a side view of an exemplary therapeutic oral appliance with an adjustable tongue retainer portion, according to some embodiments of the present disclosure.
Figure 15B:
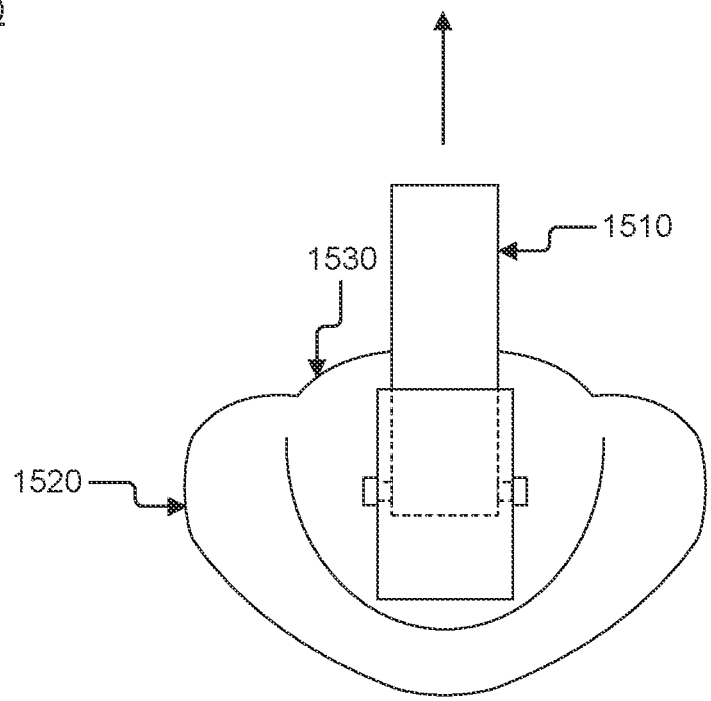
FIG. 15B illustrates a top-down view of an exemplary therapeutic oral appliance with an adjustable tongue retainer portion, according to some embodiments of the present disclosure.

Referring now to FIGS. 15A-15B, an exemplary therapeutic oral appliance 1500 with an adjustable tongue retainer portion 1510 is illustrated. In some embodiments, the tongue retainer portion 1510 may comprise an upper surface, a lower surface, and a longitudinal length. In some aspects, the tongue retainer portion 1510 may extend into the throat at a variety of lengths that are determined by a plurality of predetermined longitudinal lengths that are adjusted in a region of the therapeutic oral appliance 1500. In some embodiments, the tongue retainer portion 1510 may be fixed to a distal end of the hard palate portion 1530. In some implementations, the tongue retainer portion 1510 may be removed from the therapeutic oral appliance 1500. This may be a helpful state for users who are beginning the acclimation process of the tongue retainer portion 1510 within the throat.

In some embodiments, the adjustable aspect of the tongue retainer portion 1510 may interface with an extrusion connected to the mouth guard portion 1520. In some aspects, the adjustment of the tongue retainer portion 1510 may comprise a mechanism that exerts force on a fixture attached to the therapeutic oral appliance 1500. In some implementations, the hard palate portion 1530 may provide stability as the therapeutic oral appliance 1500 is adjusted within the oral cavity. In some aspects, the tongue retainer portion 1510 may comprise an airway 1515 that extends in conjunction with the extension of the tongue retainer portion 1510.

In some embodiments, the airway 1515 may originate on the top of the mouth guard portion 1520. In some implementations, the airway 1515 and tongue retainer portion 1520 may be molded to follow the contour of the hard palate and soft palate. In some aspects, one or more channels for airway patency are included along the sides of airway 1515. In some embodiments, these channels may begin between the teeth or gums, as non-limiting options, in the case of edentulism, to provide airway patency so the airway 1515 is not occluded by the teeth or lips.

In some embodiments, the airway 1515 and the tongue retainer portion 1520 may comprise a reinforced bridge portion that runs along the midline, near the midline, or parallel to midline of the hard palate and soft palate, as non-limiting alternatives. In some implementations, this reinforced portion may be attached to a flattened section that runs parallel to the hard palate portion 1530. This may provide increased surface area to push and stabilize the tongue and soft palate tissue away from each other to provide an airway 1515. In some aspects, the gap created by the reinforced bridge between the palate and the flattened plane may facilitate air flow. In some embodiments, the parallel planes separated by the reinforced bridge may form the airway 1515.

As an illustrative example, the cross section of this structural design may be similar to an I-beam. The I-beam consists of two horizontal planes, known as flanges, connected by one vertical component, or the web. The shape of the flanges and the web create an "I" cross-section. The flanges correlate to the planes touching the palate on one end and the tongue on the other end. The web correlates to the reinforced bridge that is the vertical component that connects the two horizontal planes. The space between the flanges created by the web is the channel where the air flow passes. The cross-sectional area for the airway 1515 may be sufficient to prevent increased respiratory effort or increased negative pressure on the lungs.

Figure 16A:
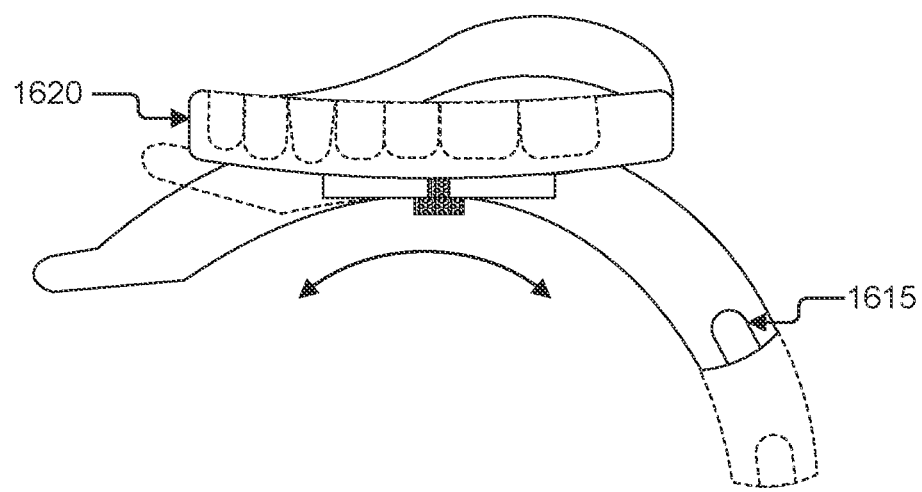
FIG. 16A illustrates a side view of an exemplary therapeutic oral appliance with an adjustable tongue retainer portion, according to some embodiments of the present disclosure.
Figure 16B:
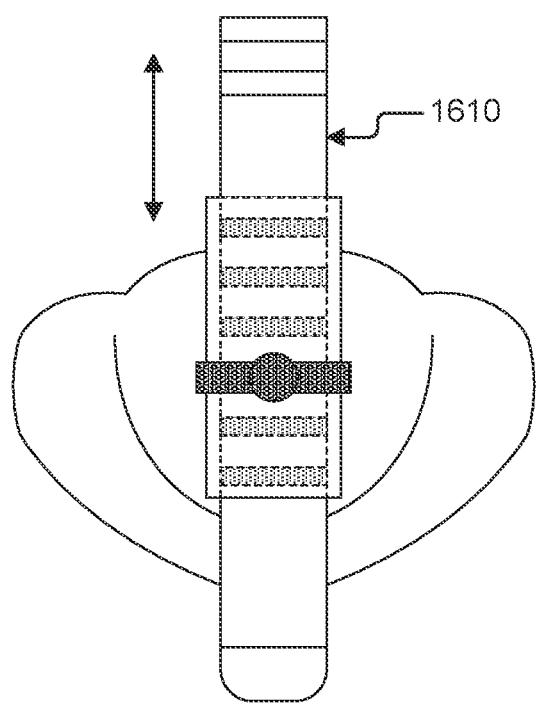
FIG. 16B illustrates a top-down view of an exemplary therapeutic oral appliance with an adjustable tongue retainer portion, according to some embodiments of the present disclosure.

Referring now to FIG. 16A-16B, an exemplary therapeutic oral appliance 1600 with an adjustable tongue retainer portion 1610 is illustrated. In some embodiments, the tongue retainer portion 1610 may comprise an upper surface, a lower surface, and a longitudinal length. In some aspects, the tongue retainer portion 1610 may extend into the throat at a variety of lengths that are determined by a plurality of predetermined longitudinal lengths that are adjusted in a region of the therapeutic oral appliance 1600. In some implementations, the tongue retainer portion 1610 may be removed from the therapeutic oral appliance 1600.

In some embodiments, the mouthguard portion 1620 may remain fixed while the airway 1615 may be moved and secured at different depths within the throat. In some implementations, the airway 1615 channel may be slid back and forth until the desired depth into the throat is reached. In some aspects, the airway 1615 may be secured into this position by a clamp or another non-limiting securing device.

For example, a client may purchase a single therapeutic oral appliance and, at first, may use the therapeutic oral appliance with an airway that is completely retracted. The client may gradually increase the extension of the airway into the throat until the airway has extended the originally intended distance into the throat.

In some embodiments, the airway 1615 may originate on the top of the mouth guard portion 1620. In some implementations, the airway 1615 and tongue retainer portion 1620 may be molded to follow the contour of the hard palate and soft palate. In some aspects, one or more channels for airway patency are included along the sides of airway 1615. In some embodiments, these channels may begin between the teeth or gums, as non-limiting options, in the case of edentulism, to provide airway patency so the airway 1615 is not occluded by the teeth or lips.

Figure 17:
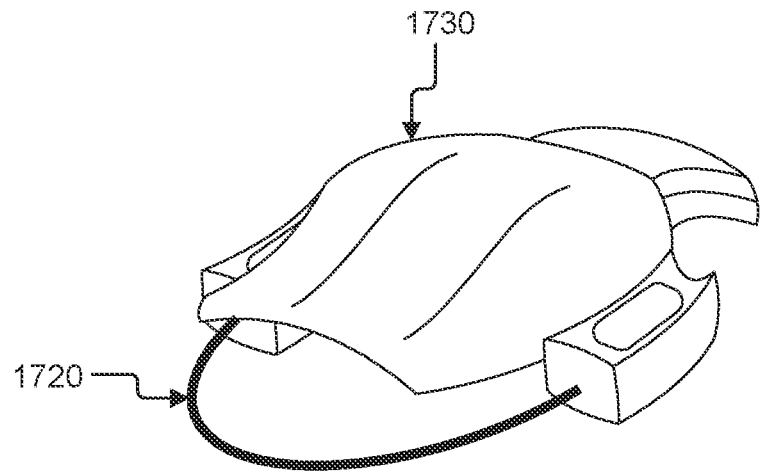
FIG. 17 illustrates an exemplary therapeutic oral appliance, according to some embodiments of the present disclosure.

Referring now to FIG. 17, an exemplary therapeutic oral appliance 1700 is illustrated. In some embodiments, the mouth guard portion 1720 may comprise a plurality of components. In some aspects, the mouth guard portion 1720 may comprise a brace with selective teeth caps. For example, at least one flexible wire may prevent slipping by applying a minimal retaining force upon the front teeth. A symmetrical plurality of tooth caps may be attached to the flexible wire and secure the therapeutic oral appliance 1700 by enclosing a plurality of teeth on both sides of the mouth.

In some embodiments, the tooth caps may comprise a generic cast that, upon inducing heat to increase malleability, may be formed to the shape of the intended teeth. In some aspects, the tooth cap may comprise a cavity designed to enclose a plurality of teeth simultaneously. The thickness of the outside edge of the tooth cap may be of minimal thickness to ensure a fit between the teeth enclosed within the tooth cap and those excluded. In some implementations, a mold may provide a mated fit between the hard palate portion 1730 and the hard palate within the oral cavity.

Figure 18:
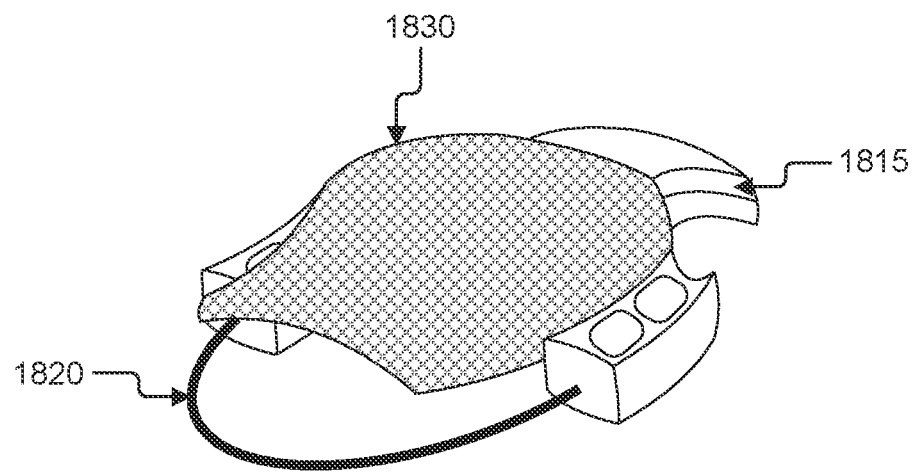
FIG. 18 illustrates an exemplary therapeutic oral appliance, according to some embodiments of the present disclosure.

Referring now to FIG. 18, an exemplary therapeutic oral appliance 1800 is illustrated. In some embodiments, the mouth guard portion 1820 may comprise a plurality of components. In some aspects, the mouth guard portion 1820 may comprise a brace with selective teeth caps. In some embodiments, the teeth caps may enclose a plurality of teeth singularly. In some implementations, the mouth guard portion 1820 may allow a user to bite down on the therapeutic oral appliance 1800 without requiring a fitting over teeth. This may allow for a more universal fit, such as for over-the-counter solutions.

For example, the teeth caps may enclose three teeth separately on both sides of the mouth to ensure the required stability and security for the therapeutic oral appliance 1800. In some implementations, a mold may provide a mated fit between the hard palate portion 1830 and the hard palate within the oral cavity. In some aspects, the hard palate portion 1830 may comprise a variety of materials to accommodate a plurality of preferences. As an example, the therapeutic oral appliance 1800 may comprise silicone for ideal softness, durability, and hygiene.

In some embodiments, the therapeutic oral appliance may comprise a soft silicone material with low shore hardness. This may provide an airway 1815 channel for breathing that allows for flexibility. The flexibility may allow the patient to swallow and maintain some tongue movement. This allowance may increase comfort for the patient. In some implementations, the mouth guard portion 1820 may cover one or more teeth or gums as a means to protect teeth from pressure points from the oral airway. The mouth guard portion 1820 may stabilize the oral airway while the user is unconscious to reduce the chance of inadvertent rejection by spitting out the therapeutic oral appliance 1800.

For example, a user's hard palate may be prone to inflammation when interfacing with typical medical grade plastics and polymers. The user may experience greater comfort and utility by utilizing a therapeutic oral appliance 1800 that comprises a hard palate portion 1830 composed of a metal or silicone mesh. A flexible or meshed hard palate portion 1830 may allow for a snug fit without requiring a custom mold.

Figure 19:
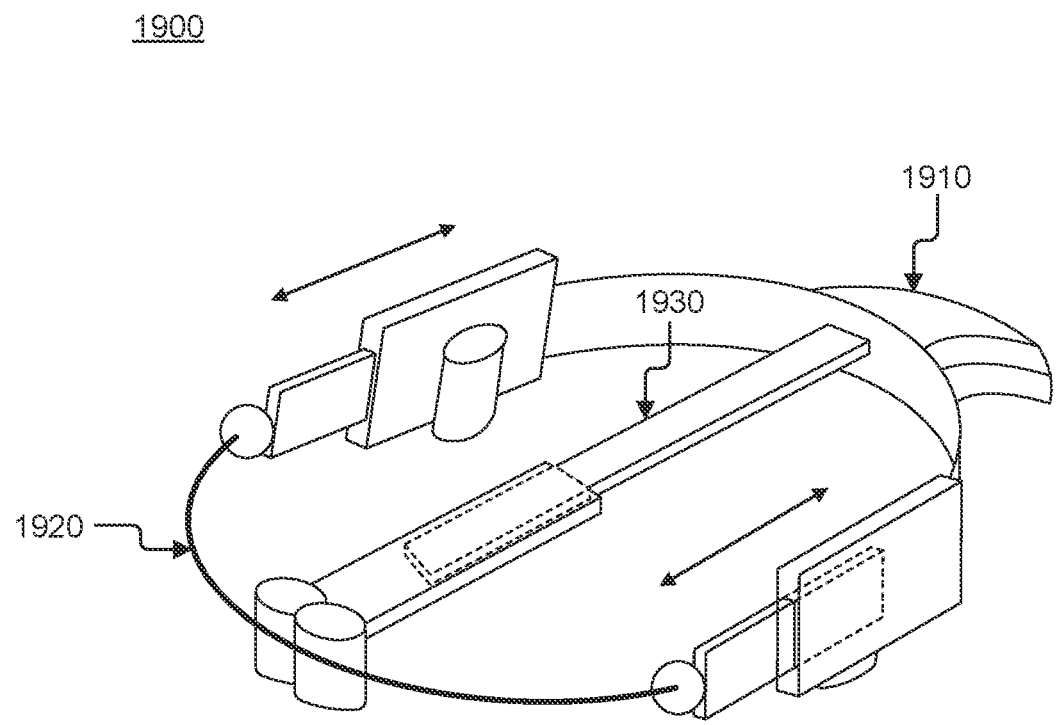
FIG. 19 illustrates an exemplary adjustable therapeutic oral appliance, according to some embodiments of the present disclosure.

Referring now to FIG. 19, an exemplary adjustable therapeutic oral appliance 1900 is illustrated. In some embodiments, the mouth guard portion 1920 may comprise a plurality of components. In some implementations, the dimensions of the therapeutic oral appliance 1900 may be adjustable. In some aspects, the tongue retainer portion 1910 may attach to a frame of the therapeutic oral appliance 1900. In some embodiments, the hard palate portion 1930 may interface with a minimized region of the hard palate.

In some implementations, a mouth may be changing and growing quickly, such as with children. Their mouth size and shape may change between incremental tongue retainer portions 1910, which may make it impractical to use one mouth mold to create the incremental therapeutic oral appliances 1900. In some aspects, a mouth guard portion 1920 may fit over a few teeth, such as front teeth and back molars, that are unlikely to shift or change drastically during the acclimation period for the therapeutic oral appliance 1900. This may be combined with an extendable hard palate portion 1930 that may allow for growth.

Figure 20:
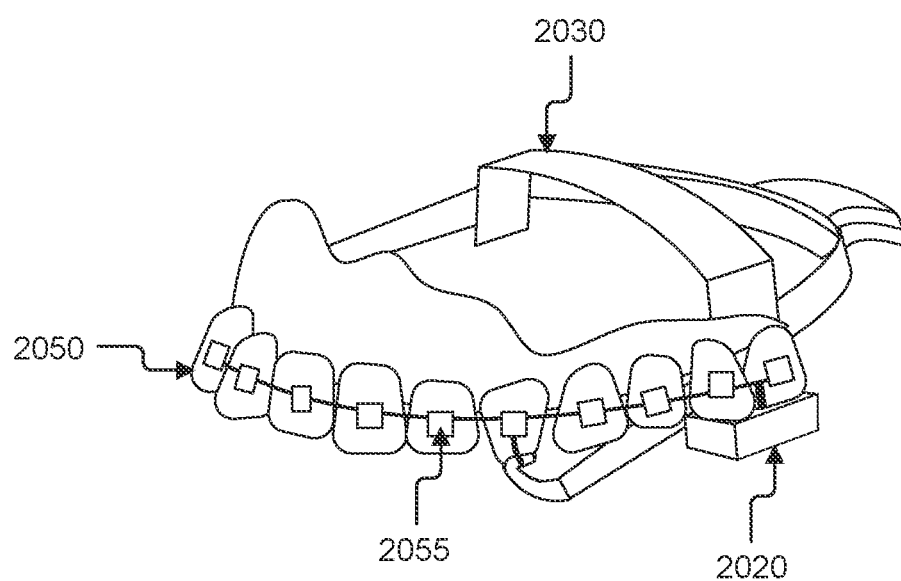
FIG. 20 illustrates an exemplary therapeutic oral appliance attachable to dental fixtures, according to some embodiments of the present disclosure.

Referring now to FIG. 20, an exemplary therapeutic oral appliance 2000 configured to interface with one or more dental fixtures, such as by being attachable thereto, is illustrated. In some aspects, the dental fixtures may be attached to the teeth 2050. For example, the therapeutic oral appliance 2000 may connect to the metal fastening rods located on braces 2055 that are secured to the teeth 2050. For example, a teenager may overcome sleep apnea while wearing braces by attaching the therapeutic oral appliance 2000 to hooks on braces attached to the canine teeth. In some embodiments, the mouth guard portion 2020 may extend rearward into the mouth. In some implementations, the hard palate portion 2030 may interface with a minimized region of the hard palate.

Figure 21:
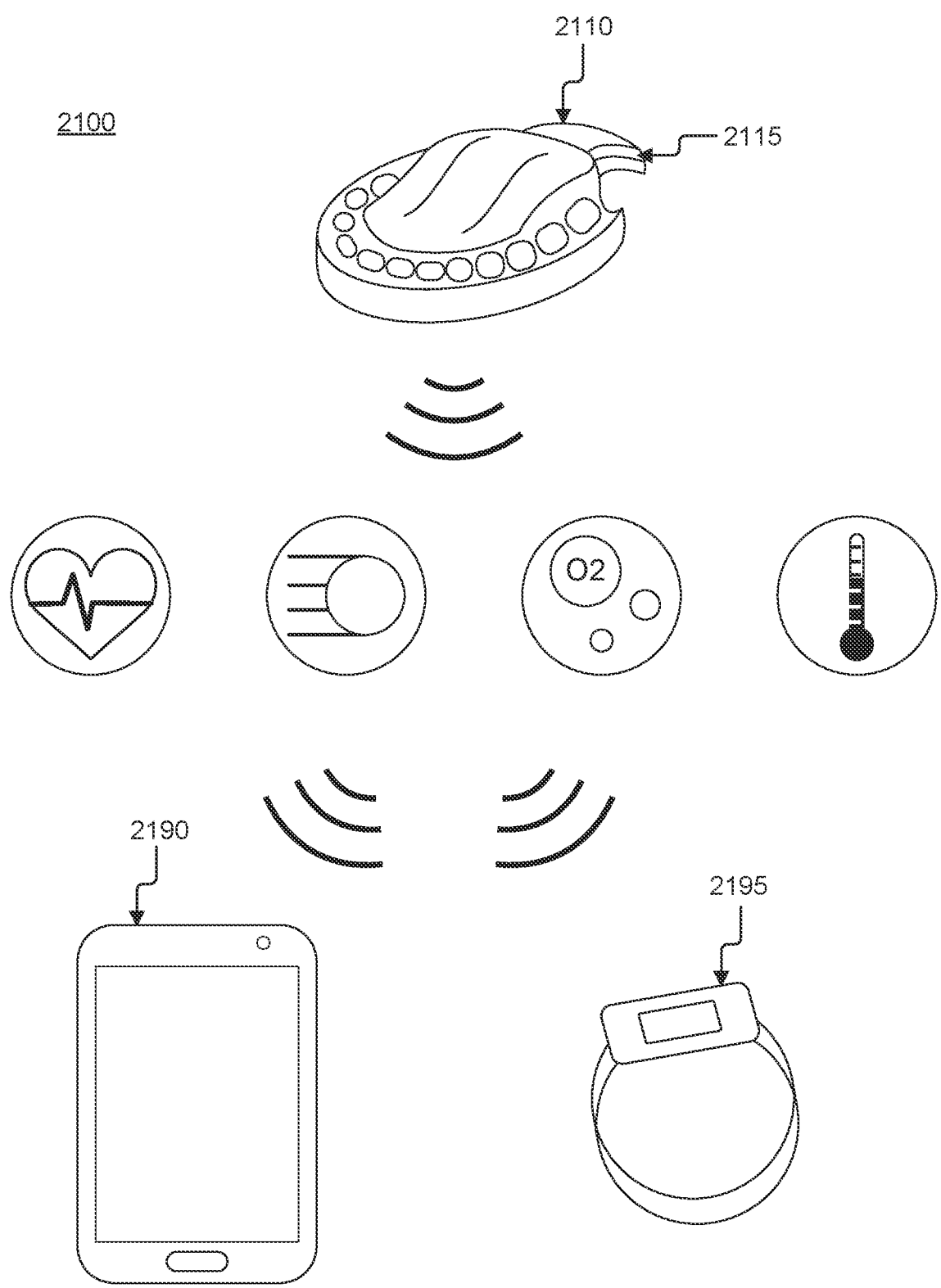
FIG. 21 illustrates an exemplary therapeutic oral appliance with wireless data transmission capabilities, according to some embodiments of the present disclosure.

Referring now to FIG. 21, an exemplary therapeutic oral appliance 2100 with wireless data transmission capabilities is illustrated. In some embodiments, the therapeutic oral appliance may contain a plurality of electronic components that may be configured to interface with at least one external device 2190. In some implementations, the therapeutic oral appliance 2100 may be configured to interface with and relay information to at least one wearable device 2195 (such as, for example and not limitation, a smart watch). In some aspects, the tongue retainer portion 2110 may comprise a one or more sensors.

In some embodiments, the airway 2115 may contain a plurality of electronic components. For example, the therapeutic oral appliance 2100 may comprise electrodes that may provide transcutaneous electrical stimulation to oropharyngeal and tongue muscles. This may increase muscle tone, allowing for an opening of the patient airway channel.

For example, a child prone to seizures may use a therapeutic oral appliance 2100 with an embedded accelerometer that notifies the parents of sharp increases in rapid movement that may be indicative of a seizure. This may be helpful at night when the family is asleep and the parents may otherwise remain unaware of the child's seizure. The therapeutic oral appliance 2100 may limit likelihood that a seizure may cause the tongue to obstruct the child's airway, which may cause permanent or temporary brain damage.

As another example, a user may purchase a therapeutic oral appliance 2100 to overcome sleep apnea that pairs with an external device 2190 in the form of the user's phone (such as, for example and not limitation, a smartphone) or computing device, such as a desktop computer, a laptop computer, or tablet as non-limiting examples. Embedded accelerometers and heart rate monitors may record information as the user sleeps to display quality of sleep information. The user may be able to see how restless they slept as well as their rest heart rate and oxygen levels. This may assist in overcoming sleep apnea by emitting vibrational frequencies during sleep to reposition the user to a better sleeping position when oxygen levels are too low.

As another example, a user may be recovering from an illness that has a high rate of respiratory issues. The therapeutic oral appliance 2100 may track oxygenation levels (for example, by using a pulse oximeter) and heart rate to monitor and manage symptoms. Where levels drop below predefined threshold parameters, a practitioner or hospital may be notified. If a user is unresponsive to the practitioner, an ambulance may be sent.

As an illustrative example, an anesthesiologist may insert a therapeutic oral appliance 2100 during a surgery that comprises one or more health monitors. The anesthesiologist may monitor heart rate, oxygen levels, and breathing rate during the surgery. This information may display via Bluetooth® connection with one or more external devices 2190 in the form of one or more medical apparatuses stationed within the operation room. The medical equipment may be configured to convey notifications and alarms for predetermined thresholds. The medical equipment may notify the anesthesiologist of recommended times to routinely evaluate specific health criterion based on current health levels of the patient.

As another illustrative example, the therapeutic oral appliance 2100 may comprise a capnograph or gas analyzer. A capnograph may measure predefined gases, such as inhaled oxygen and expired carbon dioxide. A gas analyzer may indicate how much oxygen therapy may be required to achieve a desired blood oxygen saturation. The gas monitors may provide indicative information regarding a patient's ventilation. Audible and visual indicators may notify the healthcare professional if there is obstruction or hypercarbic symptoms due to OSA or poor ventilation.

Figure 22A:
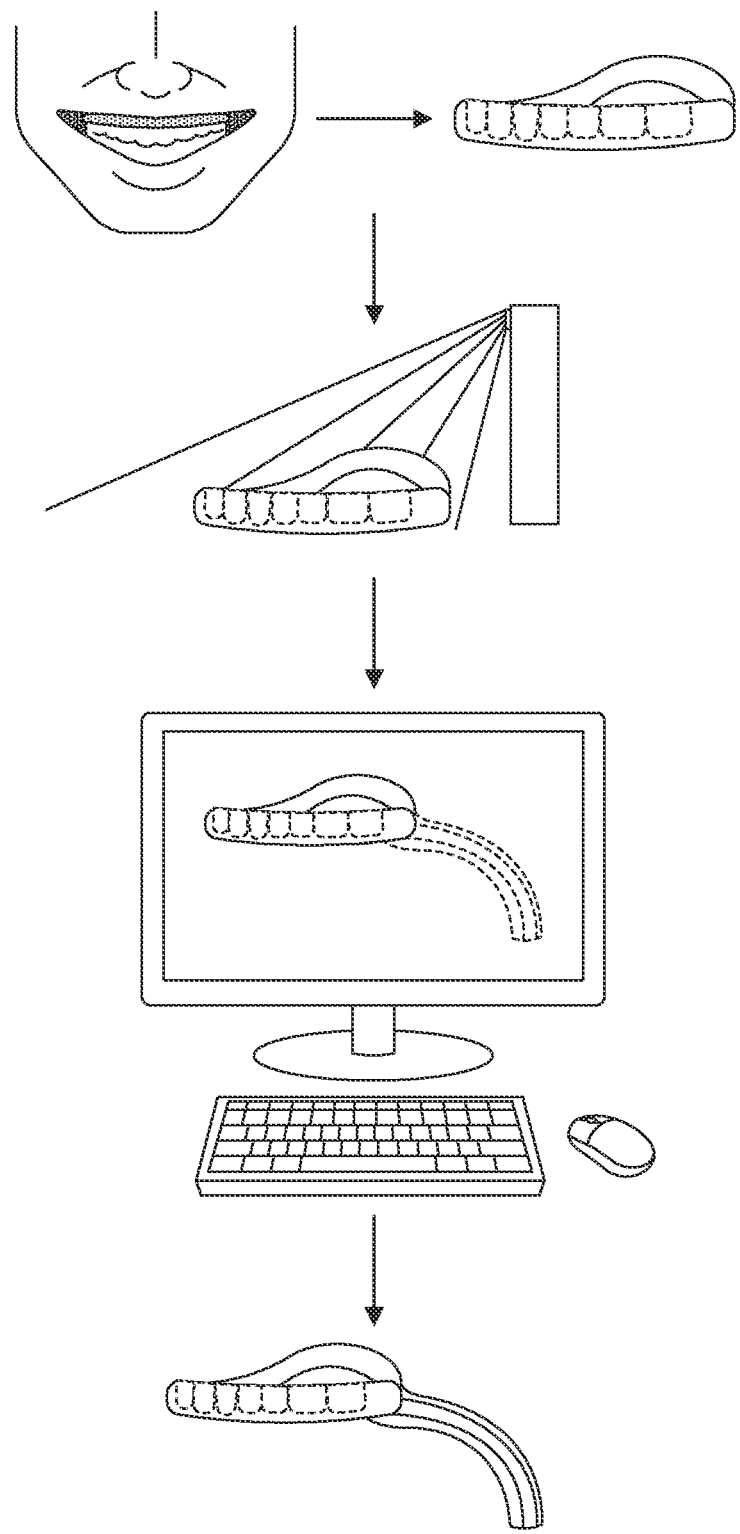
FIG. 22 illustrates a process of forming an exemplary therapeutic oral appliance, according to some embodiments of the present disclosure.
Figure 22B:
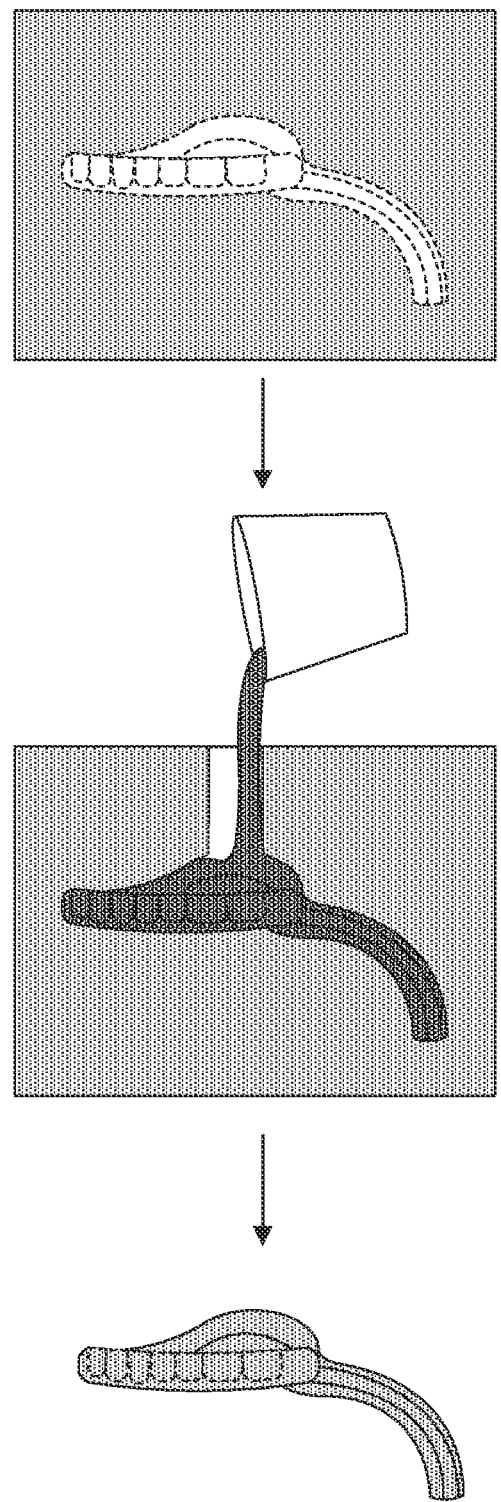

Referring now to FIGS. 22A-22B, a process 2200 of forming an exemplary therapeutic oral appliance is illustrated. In some embodiments, therapeutic oral appliance may be formed from an impression. In some implementations, the impression may comprise an impression of teeth and an impression of the hard palate, as non-limiting options. For example, physical impressions may be made of the upper hard palate, dentition, and as much of the soft palate as can be tolerated.

In some aspects, the impressions of the patient's mouth may be rendered digitally. As an example, an impression may be scanned by a high-fidelity 3-D scanner to render a virtual representation of the impression within a modeling software. In some embodiments, a digital rendering of an airway may be created along the longitudinal length of the digital impression of the therapeutic oral appliance. In some implementations, a physical construction of the digital rendering and airway may be formed. For example, the digital rendering may be printed by a 3-D printer. In some embodiments, this physical construction may provide a tangible medium to further the formation of the therapeutic oral appliance, such as by providing a shape for a mold.

In some aspects, a mold may be formed using the physical rendition of the impression and the airway. In some embodiments, the mold may be used to create a therapeutic oral appliance by using the mold for casting. For example, a 3-D printed prototype may be place in casting clay to form an impression that is subsequently filled with a soft silicone material. As another example, a synthetic polymer may be poured into the mold and, upon solidifying, may produce a therapeutic oral appliance in the form of the impression and the airway.

Figure 23:
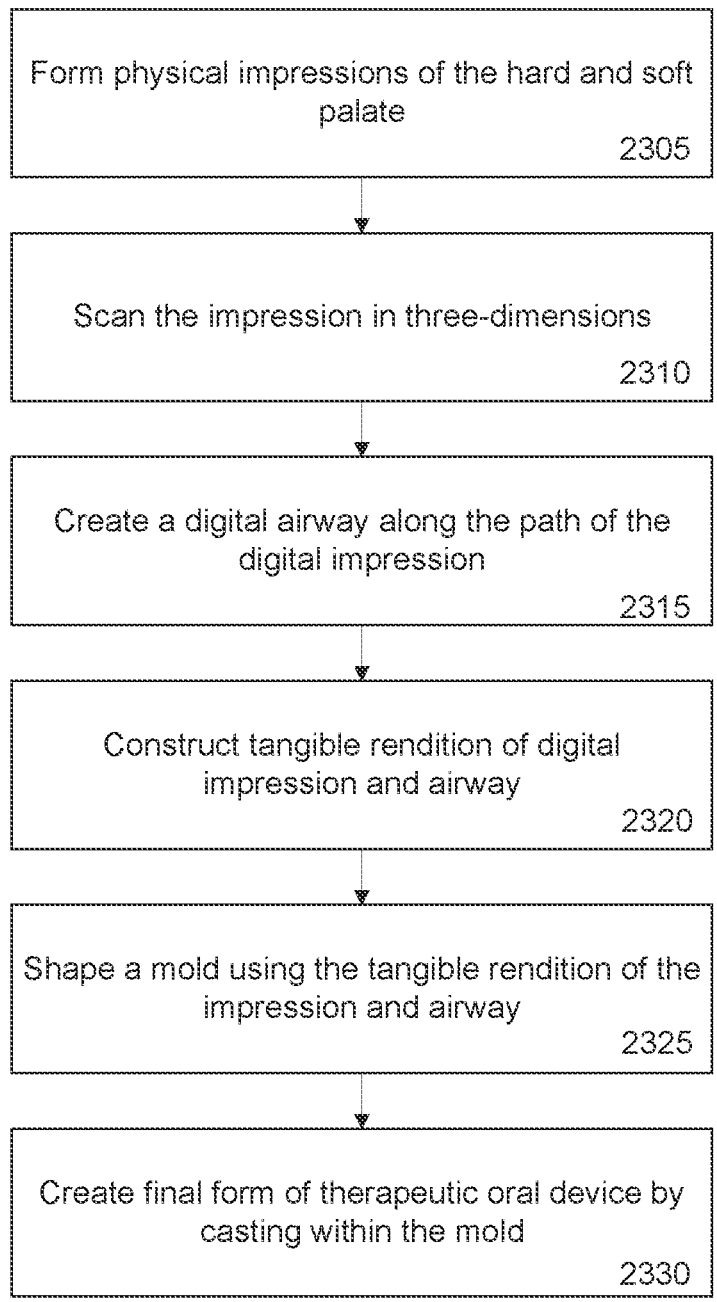
FIG. 23 illustrates a process of forming an exemplary therapeutic oral appliance, according to some embodiments of the present disclosure.

Referring now to FIG. 23, a method 2300 of forming an exemplary therapeutic oral appliance is illustrated. At 2305, physical impressions of a patient's mouth may be formed. In some embodiments, the impressions may comprise an impression of the teeth and an impression of the hard palate, as non-limiting options. At 2310, the impressions of the patient's mouth may be scanned in three dimensions. As an example, an impression may be scanned by a high-fidelity 3-D scanner to render a virtual representation of the impression within a modeling software.

At 2315, a digital rendering of an airway may be created along the longitudinal length of the digital impression. At 2320, a physical construction of the digital impression and airway may be constructed. For example, the digital rendering of the impression and the airway may be printed by a 3-D printer.

At 2325, a mold may be formed using the physical rendition of the impression and the airway. At 2330, the mold may be used to create a therapeutic oral appliance by using the mold for casting. For example, a synthetic polymer may be poured into the mold and, upon solidifying, may produce a therapeutic oral appliance in the form of the impression and the airway.

Figure 24:
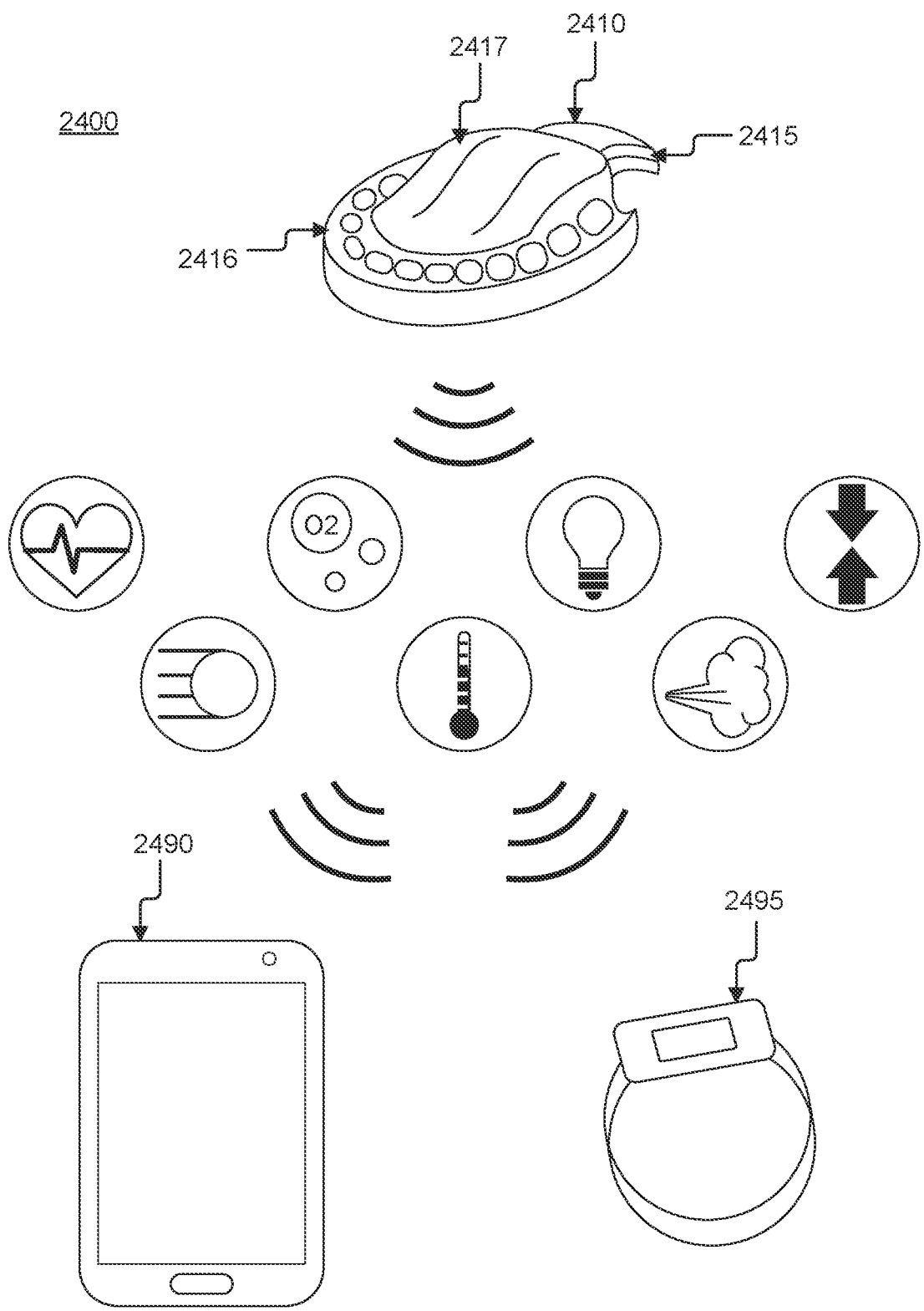
FIG. 24 illustrates an exemplary therapeutic oral appliance with wireless data transmission capabilities, according to some embodiments of the present disclosure.

Referring now to FIG. 24, an exemplary therapeutic oral appliance 2400 with wireless data transmission capabilities, according to some embodiments of the present disclosure, is illustrated. In some embodiments, the therapeutic oral appliance 2400 may comprise one or more electronic components, wherein at least one of the electronic components may be configured to interface with at least one external device 2490. In some implementations, the therapeutic oral appliance 2400 may be configured to interface with at least one wearable technology device 2495 (such as, for example and not limitation, a smart watch). In some aspects, the one or more electronic components of the therapeutic oral appliance 2400 may enable the therapeutic oral appliance 2400 to transmit data to and/or receive data from the external device 2490 and/or the wearable technology device 2495.

In some aspects, at least one internal or external portion of at least one of: a tongue retainer portion 2410, a mouth guard portion 2416, a hard palate portion 2417, or any other appropriate portion of the therapeutic oral appliance 2400 may comprise one or more electronic components in the form of one or more sensors and/or one or more electrodes. In some embodiments, one or more electrical wires may be placed upon at least a portion of at least one external surface of the therapeutic oral appliance 2400 and/or at least partially embedded within at least one internal portion of the therapeutic oral appliance 2400. As a non-limiting example, one or more electrical wires may be embedded inside the therapeutic oral appliance 2400 to block contact between the electrical wire(s) and the inside of a user's mouth to minimize the user's likelihood of experiencing irritation or encountering injury, as well as increase the useful longevity of the therapeutic oral appliance 2400.

In some embodiments, one or more electrical wires may be used to couple two or more electronic components together, such as, for example and not limitation, to couple one or more sensors or electrodes to each other and/or to one or more batteries or other power sources. In some implementations, the therapeutic oral appliance 2400 may comprise one or more transmitting devices and/or one or more receiving devices for transmitting or receiving data, respectively. By way of example and not limitation, each transmitting device may comprise at least one of: a radiofrequency (RF) transmitter or a Bluetooth® transmitter, and each receiving device may comprise at least one of: an RF receiver and a Bluetooth® receiver. In some aspects, one or more electrical wires may couple each transmitting device and/or each receiving device to one or more sensors and/or one or more electrodes, as well as to at least one power source, such as, for example and not limitation, a battery. In some embodiments, the transmitting device(s) of the therapeutic oral appliance 2400 may transmit data obtained from one or more sensors and/or one or more electrodes to at least one of: the external device 2490, the wearable technology device 2495, or at least one external or remote database or similar memory resource for at least temporary storage therein.

In some embodiments, one or more sensors or electrodes within or upon the therapeutic oral appliance 2400 may comprise at least one of: one or more electromyography electrodes, one or more acceleromyography sensors, one or more piezoelectric myography sensors, one or more temperature sensors, one or more peripheral artery tonometry sensors, one or more photoplethysmography sensors, one or more pulse oximetry sensors, one or more moisture sensors, one or more pH sensors, one or more audio sensors, one or more force sensors, one or more light-emitting sensors, one or more light absorption sensors, one or more muscle movement sensors, one or more accelerometers, one or more heart rate monitors, and/or one or more capnography sensors.

In some embodiments, one or more sensors and/or electrodes may be configured upon or within the therapeutic oral appliance 2400 at a location that may be most advantageous to its purpose. As a non-limiting example, one or more temperature sensors, such as a thermometer, may be configured proximate to a deeper region within a user's oral cavity, such as at or near the distal end of the tongue retainer portion 2410, thus allowing the temperature sensor(s) to obtain measurements closer to a core region of the user's body, thereby improving the accuracy of the measurements.

In some non-limiting exemplary embodiments, the functionality of one or more sensors of the therapeutic oral appliance 2400 may be at least partially dependent on emitting light and/or measuring light absorption, such as may be the case with one or more pulse oximetry sensors; therefore, it may be advantageous to configure such sensor(s) proximate to one or more thin membranes of the upper hard and/or soft palate, and so such sensor(s) may be arranged upon or within at least one portion of the therapeutic oral appliance 2400 adjacent thereto, such as, for example and not limitation, upon or within a superior surface of the tongue retainer portion 2410 and/or the hard palate portion 2417. Additionally, in some implementations, the therapeutic oral appliance 2400 may comprise one or more at least partially opaque materials or structures to block ambient light from interfering with the performance or functionality of any sensor(s) and/or electrode(s) that may be at least partially dependent on emitting or absorbing light.

In some aspects, the therapeutic oral appliance 2400 may comprise one or more sensors configured to measure the movement of one or more muscles within a user's mouth, throat, or oral cavity. By way of example and not limitation, such sensor(s) may be located upon or within one or more portions of the tongue retainer portion 2410 to measure interactions between the therapeutic oral appliance 2400 and the user's tongue or soft palate.

In some implementations, one or more sensors may be configured to measure a user's bite force, wherein the sensor(s) may be located at or near one or more external or internal portions of the mouth guard portion 2416 of the therapeutic oral appliance 2400 to detect and measure an amount of force applied to the mouth guard portion 2416 when at least a portion of the mouth guard portion 2416 experiences physical contact from at least a portion of the user's upper teeth and at least a portion of the user's lower teeth in a substantially simultaneous manner.

By way of example and not limitation, sensor(s) for measuring a user's bite force may comprise one or more of: at least one strain gauge transducer, at least one piezoresistive transducer, at least one pressure transducer, at least one piezoelectric transducer, at least one pressure sensitive film, or at least one optical sensor, as well as any other appropriate sensing device(s). In some aspects, one or more sensors configured to detect or measure airway channel occlusion for a user may be located at or near one or more internal or external portions of the mouth guard portion 2416 of the therapeutic oral appliance 2400.

In some aspects, the therapeutic oral appliance 2400 may comprise one or more materials that may facilitate the functionality or performance of one or more sensors or electrodes configured therewith. As a non-limiting example, the therapeutic oral appliance 2400 may at least partially comprise at least one optically transparent material to prevent interference of the functionality of at least one pulse oximetry sensor.

In some embodiments, the therapeutic oral appliance 2400 may comprise one or more electrodes that may be configured to facilitate transcutaneous electrical nerve or electrical muscle stimulation. As a non-limiting example, one or more electrodes may be located within or upon one or more portions of an inferior or superior surface of the therapeutic oral appliance 2400 to help strengthen and tone one or more muscles within a user's mouth, throat, or oral cavity, such as, for example and not limitation, the user's upper airway dilator muscles and/or the user's tongue muscles. In some aspects, each of the one or more electrodes may at least partially comprise and/or may be at least partially embedded within one or more electrically conductive materials. In some non-limiting exemplary embodiments, the one or more electrodes may at least partially comprise and/or may be at least partially embedded within one or more of: carbon-infused medical grade silicone rubber, one or more carbon nanotube silicone composites, polydimethylsiloxane (PDMS), or one or more PDMS composites including those that may be combined with nickel, carbon nanotubes, and/or silver, as non-limiting examples.

In some aspects, at least one airway 2415 of the therapeutic oral appliance 2400 may comprise one or more electronic components. By way of example and not limitation, the airway 2415 may comprise one or more electrodes that may be configured to facilitate transcutaneous electrical stimulation to one or more oropharyngeal and/or tongue muscles of a user. In some implementations, this stimulation may facilitate an increase in muscle tone, thereby promoting opening of the user's airway channel.

In some aspects, the therapeutic oral appliance 2400 may comprise one or more electrodes 2480 configured to facilitate neuromuscular electrical stimulation. By way of example and not limitation, such neuromuscular electrical stimulation may be implemented in conjunction with one or more sensors 2401 in the form of capnography sensors, respiratory sensors, thoracic sensors, and/or other breathing sensors. In some embodiments, when one or more of these sensors 2401 may detect that a user is not breathing or that the user's breathing is at least partially obstructed, the one or more neuromuscular electrical stimulation electrodes 2480 may be configured to send at least one electrical pulse that may cause the user's tongue and/or upper airway dilator muscles to contract at least partially to facilitate opening of the user's airway passage.

In some implementations, the therapeutic oral appliance 2400 may be used to alleviate one or more health concerns for a user, such as sleep apnea. In some aspects, neuromuscular electrical stimulation provided by one or more electrodes 2480 of the therapeutic oral appliance 2400 may facilitate an increase in muscle tone within the user's mouth, oral cavity, or throat, thereby reducing sleep apnea symptoms. In some non-limiting exemplary embodiments, this increase in muscle tone may allow the size of the center portion (or web) of the airway channel 2415 and/or a cross section of the tongue retainer portion 2410 to be incrementally and gradually decreased overtime, such as, for example and not limitation, by being compressed or compacted in an adjustable manner, by being replaced by a succession of one or more modular components, or by using a plurality of therapeutic oral appliances 2400 of different sizes. By way of example and not limitation, the gradual reduction of the size of the center portion of the airway channel 2415 or the tongue retainer portion 2410 may result in increased user comfort.

In some embodiments, one or more electrodes 2480 for facilitating neuromuscular electrical stimulation may be configured within or upon one or more portions of the therapeutic oral appliance 2400 at a location that may be advantageous to its purpose or functionality, which may be to assist a user in overcoming sleep apnea, as a non-limiting example. In some aspects, one or more neuromuscular electrical stimulation electrodes 2480 may be located on any portion(s) of the therapeutic oral appliance 2400 that may at least partially contact a user's tongue, such as, for example and not limitation, the tongue retainer portion 2410. By way of example and not limitation, at least one neuromuscular electrical stimulation electrode 2480 may be placed upon or near the user's chin to facilitate stimulation of the genioglossus muscle. As a non-limiting example, the simulation of the genioglossus muscle may cause the tongue to tighten and at least partially protrude from the user's mouth, thereby increasing the opening of the user's airway channel. In some aspects, this direct stimulation of the genioglossus muscle may produce an effect similar to that facilitated by hypoglossal nerve stimulators without the need for any surgical implants.

In some embodiments, the one or more neuromuscular electrical stimulation sensors may be configured within or upon the therapeutic oral appliance 2400 at a location that may be advantageous to its purpose or functionality, which may be to overcome sleep apnea. As a non-limiting example, the one or more neuromuscular electrical stimulation sensors may be located on any portion of the therapeutic oral appliance that comes into contact with the tongue. As a non-limiting example, the one or more neuromuscular electrical stimulation sensors may be located near the chin to allow stimulation of the genioglossus muscle. As a non-limiting example, the simulation of the genioglossus muscle may cause the muscle to tighten and protrude, opening the airway. As an illustrative example, a child prone to seizures may use a therapeutic oral appliance 2400 with an embedded accelerometer connected to a Bluetooth® transmitter that may send one or more notifications to at least one external device 2490 in the form of a smartphone that may inform the child's parents of sharp increases in rapid movement that may be indicative of a seizure. This information may be helpful at night when the family is asleep, and the parents may otherwise remain unaware of the child's seizure. In this manner, the therapeutic oral appliance 2400 may limit the likelihood that a seizure may cause the tongue to obstruct the child's airway, which may cause permanent or temporary brain damage.

As another example, a user may purchase a therapeutic oral appliance 2400 to overcome sleep apnea, wherein the therapeutic oral appliance 2400 may pair with at least one external device 2490 in the form of the user's phone (such as, for example and not limitation, a smartphone) or computing device, such as a desktop computer, a laptop computer, or tablet, as non-limiting examples, via a Bluetooth® or similar connection. One or more accelerometers and heart rate monitors embedded within one or more portions of the therapeutic oral appliance 2400 may detect and record data as the user sleeps to determine and present quality of sleep information to the user. Using this information, the user may be able to see how restlessly they slept as well as the user's rest heart rate and oxygen levels throughout the night. To assist the user in overcoming sleep apnea, the therapeutic oral appliance 2400 may comprise one or more electrodes or similar mechanisms configured to emit one or more vibrational frequencies that may prompt the user to reposition to a better sleeping position when oxygen levels may drop below a minimum threshold.

As another example, a user may be recovering from an illness that may include substantial respiratory issues. In such aspects, the therapeutic oral appliance 2400 may be configured to monitor the user's oxygenation levels (for example, by using at least one pulse oximeter) as well as the user's heart rate (such as by using a heart rate monitor) to monitor and manage the user's symptoms. In some implementations, when the user's oxygen levels, heart rate, or other health aspects drop below one or more predefined threshold parameters, a medical practitioner or hospital may be notified via at least one transmitting device upon or within a portion of the therapeutic oral appliance 2400.

In some embodiments, a medical professional may attempt to communicate with the user via at least one audio emitting device within or upon the therapeutic oral appliance 2400, wherein the audio emitting device may be electronically coupled, such as, for example and not limitation, via at least one electrical wire, to at least one power source and at least one receiving device configured to receive incoming communication data from the medical professional. In some aspects, if the user does not respond to the medical professional, such as, for example and not limitation, via a microphone or similar mechanism within or upon the therapeutic oral appliance 2400 and electronically coupled to the transmitting device and the power source(s), an ambulance or other emergency vehicle may be sent to the user's location as may be determined by at least one geolocation device within or upon the therapeutic oral appliance 2400.

As another illustrative example, an anesthesiologist may insert a therapeutic oral appliance 2400 within a user's oral cavity during a surgery, wherein the therapeutic oral appliance 2400 may comprise one or more sensors in the form of one or more health monitors. This may enable the anesthesiologist to use the therapeutic oral appliance 2400 to monitor the user's heart rate, oxygen levels, breathing rate, and/or other health aspects during the surgery. In some aspects, the user's health information may be displayed upon one or more external devices 2490 via a Bluetooth® connection, wherein the external device(s) 2490 may comprise one or more medical apparatuses stationed within the operation room.

In some implementations, the medical equipment may be configured to convey one or more notifications or alarms when one or more of the user's health aspects reach one or more predetermined thresholds. In some embodiments, the medical equipment may notify the anesthesiologist of recommended times to routinely evaluate specific health criterion of the user based on one or more current health levels of the user.

As a further illustrative example, the therapeutic oral appliance 2400 may comprise at least one sensor in the form of a capnography sensor or gas analyzer. In some aspects, a capnography sensor within or upon the therapeutic oral appliance 2400 may measure one or more predefined gases, such as oxygen inhaled and/or carbon dioxide exhaled by a user. In some implementations, a gas analyzer within or upon the therapeutic oral appliance 2400 may indicate how much oxygen therapy may be required to achieve a desired blood oxygen saturation for a user. In some aspects, these or similar gas monitors may provide indicative information regarding a user's ventilation.

In some non-limiting exemplary embodiments, one or more transmitting devices upon or within the therapeutic oral appliance 2400 may communicate data to one or more external devices 2490 and/or wearable technology devices 2495 to cause the external device(s) 2490 and/or wearable technology device(s) 2495 to emit one or more audible and/or visual indicators that may notify at least one healthcare professional if a user may be experiencing airway obstruction or hypercarbic symptoms due to OSA or poor ventilation.

Figure 25A:
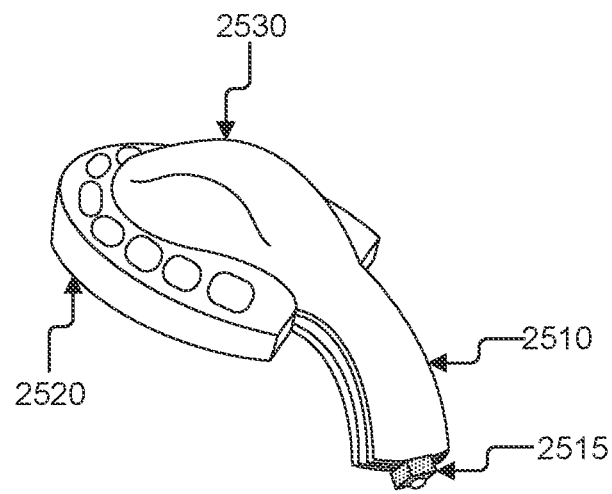
FIG. 25A illustrates an exemplary therapeutic oral appliance comprising a tongue retainer portion, according to some embodiments of the present disclosure.
Figure 25B:
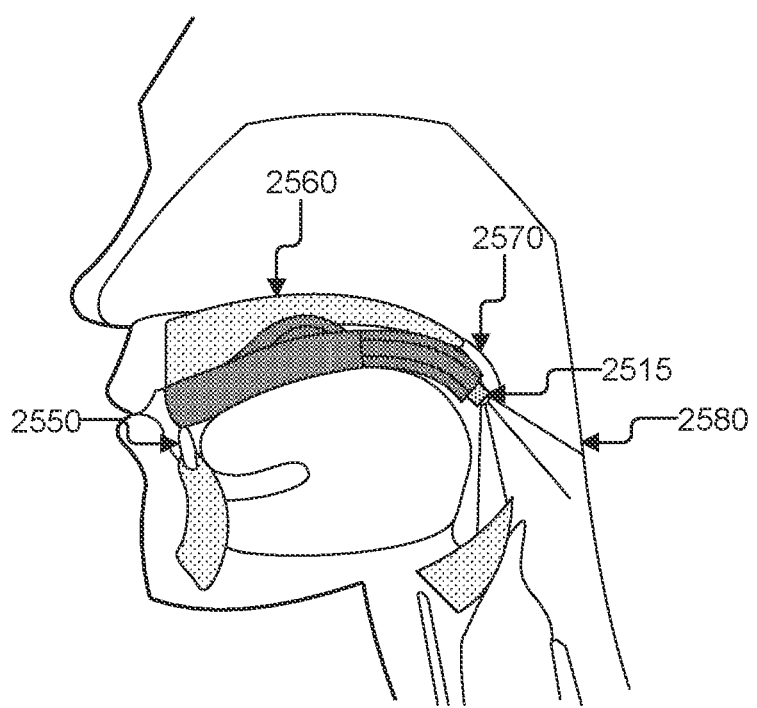
FIG. 25B illustrates a a sectional view of an oral cavity comprising an exemplary therapeutic oral appliance, according to some embodiments of the present disclosure.

Referring now to FIGS. 25A and 25B, an exemplary therapeutic oral appliance 2500 comprising a tongue retainer portion 2510, 2570, and an oral cavity comprising a therapeutic oral appliance 2500, according to some embodiments of the present disclosure, are illustrated. In some aspects, the therapeutic oral appliance 2500 may comprise a tongue retainer portion 2510, 2570; a mouth guard portion 2520, 2550; and/or a hard palate portion 2530, 2560 that may comprise one or more electronic components in the form of one or more sensors and/or one or more electrodes. In some embodiments, one or more electrical wires may be configured upon or embedded within one or more external or internal portions of the therapeutic oral appliance 2500.

As a non-limiting example, one or more electrical wires may be embedded within the therapeutic oral appliance 2500 so that the electrical wire(s) are blocked from physically contacting one or more interior portions of a user's mouth, thereby minimizing the likelihood of the user experiencing discomfort or injury and minimizing damage to the therapeutic oral appliance 2500. In some embodiments, one or more electrical wires may be used to electronically couple one or more sensors or electrodes to each other, to at least one power source (such as, for example and not limitation, a battery), to at least one transmitting device (such as, for example and not limitation, an RF transmitter or Bluetooth® transmitter, and/or to at least one receiving device (such as, for example and not limitation, an RF receiver or a Bluetooth® receiver). In some non-limiting exemplary embodiments, the therapeutic oral appliance 2500 may be configured to transmit data obtained from one or more sensors and/or one or more electrodes to at least one external device, at least one wearable technology device, and/or at least one database.

In some aspects, the therapeutic oral appliance 2500 may comprise one or more sensors or electrodes that may comprise at least one of: one or more electromyography electrodes, one or more acceleromyography sensors, one or more piezoelectric myography sensors, one or more temperature sensors, one or more peripheral artery tonometry sensors, one or more photoplethysmography sensors, one or more pulse oximetry sensors, one or more moisture sensors, one or more pH sensors, one or more audio sensors, one or more force sensors, one or more light-emitting sensors, one or more light absorption sensors, one or more muscle movement sensors, one or more accelerometers, one or more heart rate monitors, and/or one or more capnography sensors.

In some embodiments, one or more sensors may be configured within or upon the therapeutic oral appliance 2500 at a location that may be advantageous to its purpose or functionality. As a non-limiting example, one or more temperature sensors (such as, for example and not limitation, one or more thermometers) may be configured proximate to a deeper region within a user's oral cavity, such as by being located within, upon, or near a distal end of the tongue retainer portion 2510, 2570, thereby allowing the temperature sensor(s) to obtain measurements closer to the user's core body region, thus increasing the accuracy of the measurements.

Figure 26:
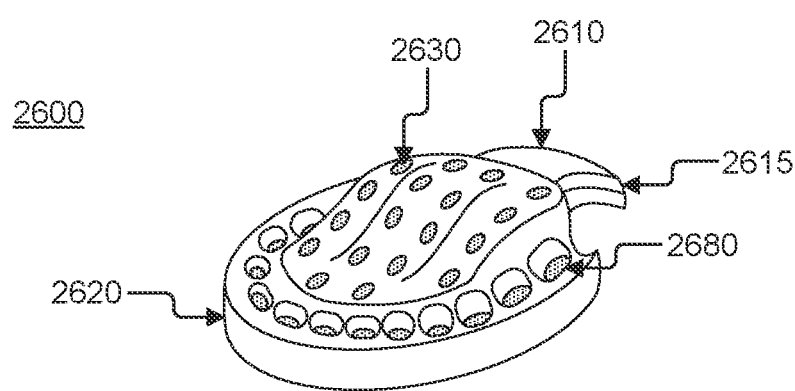
FIG. 26 illustrates a perspective view of an exemplary therapeutic oral appliance, according to some embodiments of the present disclosure.

Referring now to FIG. 26, a perspective view of an exemplary therapeutic oral appliance 2600, according to some embodiments of the present disclosure, is illustrated. In some embodiments, the therapeutic oral appliance 2600 may comprise one or more electrical wires that may be attached to one or more electrodes 2680. In some implementations, the one or more electrical wires may be connected to at least one power source, such as, by way of example and not limitation, at least one battery. In some aspects, the therapeutic oral appliance 2600 may comprise one or more transmitting devices, such as, for example and not limitation, one or more RF transmitters or Bluetooth® transmitters, wherein the transmitting device(s) may be connected to the one or more electrical wires to facilitate electronic coupling to the at least one power source and the one or more electrodes 2680. In some embodiments, the therapeutic oral appliance 2600 may transmit data obtained from the one or more electrodes 2680 to at least one external device, at least one wearable technology device, and/or at least one database or similar memory resource via the one or more transmitting devices. By way of example and not limitation, each of the one or more electrodes 2680 may comprise an electromyography electrode or any similar mechanism.

In some aspects, the therapeutic oral appliance 2600 may comprise a tongue retainer portion 2610, a mouth guard portion 2620, and/or a hard palate portion 2630 that may comprise one or more electrodes 2680. In some embodiments, the therapeutic oral appliance 2680 may comprise one or more electrodes 2680 configured to facilitate transcutaneous electrical nerve or electrical muscle stimulation. As a non-limiting example, one or more electrodes 2680 may be configured within or upon one or more portions of an inferior and/or superior surface of the therapeutic oral appliance 2600 to facilitate the strengthening and toning of one or more of a user's upper airway dilator muscles, tongue muscles, and/or other muscles.

In some aspects, each of the one or more electrodes 2680 may at least partially comprise and/or may be at least partially embedded within one or more electrically conductive materials. In some aspects, by way of example and not limitation, each of the one or more electrodes 2680 may at least partially comprise and/or may be at least partially embedded within a material that comprises at least one of: carbon-infused medical grade silicone rubber, one or more carbon nanotube silicone composites, PDMS, or one or more PDMS composites, including those in combination with nickel, carbon nanotubes, and/or silver.

In some embodiments, at least one airway 2615 of the therapeutic oral appliance 2600 may comprise one or more electrodes 2680 that may be configured to provide transcutaneous electrical stimulation to one or more oropharyngeal and/or tongue muscles of a user. In some aspects, this stimulation may cause an increase in muscle tone that may facilitate the opening of the user's oral airway channel. In some non-limiting exemplary embodiments, the electrical stimulation produced by one or more electrodes 2680 may be strong enough to be sensed by a user so as to prompt or stimulate the user to perform an action. As an illustrative example, a person prone to snoring may use a therapeutic oral appliance 2600 with one or more embedded electrodes 2680 that generate a subtle electrical impulse in the form of a slight shock or vibration that wakes the user when snoring may be detected, such as via at least one sensor in the form of a microphone or other audio capturing device.

Figure 27A:
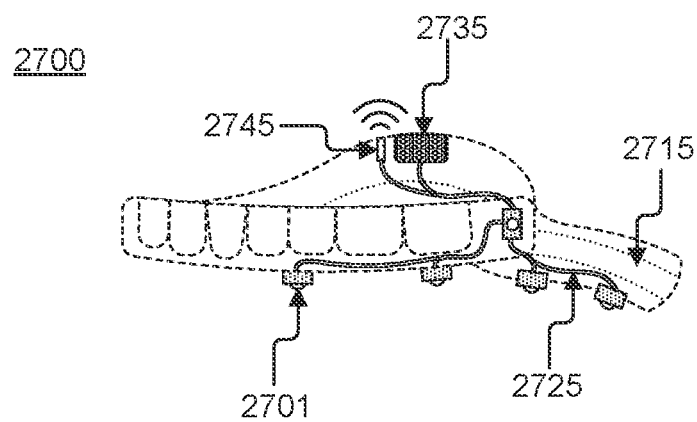
FIG. 27A illustrates an exemplary therapeutic oral appliance, according to some embodiments of the present disclosure.
Figure 27B:
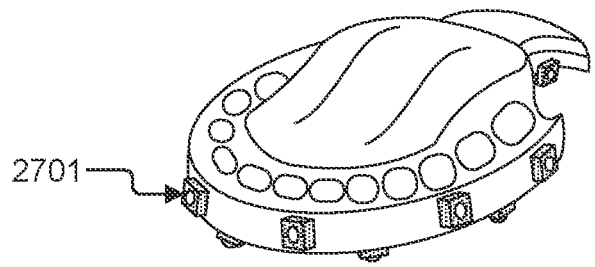
FIG. 27B illustrates a perspective view of an exemplary therapeutic oral appliance, according to some embodiments of the present disclosure.
Figure 27C:
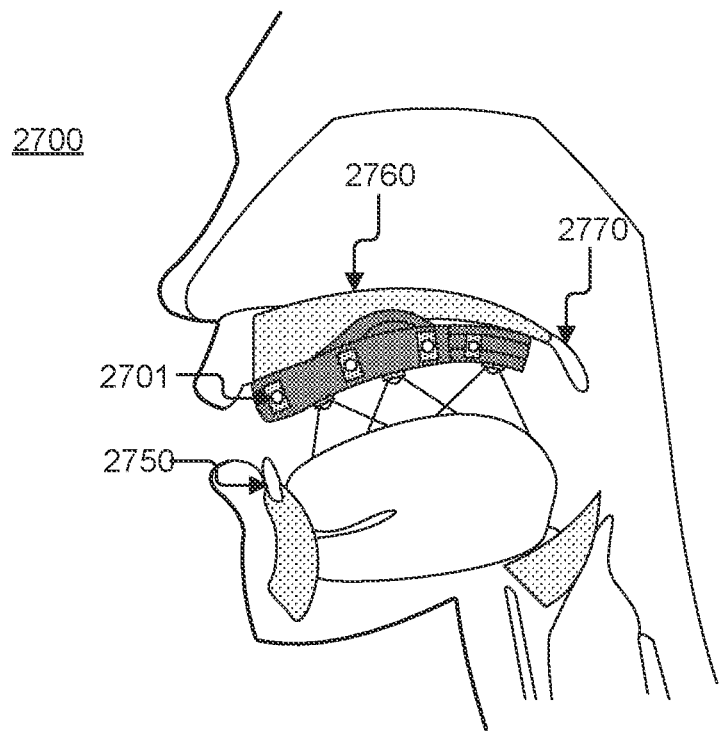
FIG. 27C illustrates a sectional view of an oral cavity comprising an exemplary therapeutic oral appliance, according to some embodiments of the present disclosure.

Referring now to FIGS. 27A, 27B, and 27C, an exemplary therapeutic oral appliance 2700, according to some embodiments of the present disclosure, is illustrated. In some aspects, the therapeutic oral appliance 2700 may comprise a tongue retainer portion 2770, a mouth guard portion 2750, and/or a hard palate portion 2760 that may comprise one or more sensors 2701. In some aspects, one or more electrical wires 2725 may be configured upon or embedded within one or more external or internal portions of the therapeutic oral appliance 2700. In some implementations, one or more electrical wires 2725 may be embedded within at least one internal portion of the therapeutic oral appliance 2700 to block the electrical wire(s) 2725 from physically contacting one or more interior portions of a user's mouth, thereby reducing the likelihood of inflicting discomfort or injury upon the user and prolonging the useful duration of the therapeutic oral appliance 2700. In some embodiments, the one or more electrical wires 2725 may be attached to one or more sensors 2701 to electronically couple the sensor(s) 2701 to each other, to at least one power source 2735 (such as, for example and not limitation, at least one battery), at least one transmitting device 2745 (such as, for example and not limitation, an RF transmitter or a Bluetooth® transmitter), and/or at least one receiving device (such as, for example and not limitation, an RF receiver or a Bluetooth® receiver).

In some non-limiting exemplary embodiments, each of the one or more sensors 2701 may comprise at least one of: one or more acceleromyography sensors, one or more piezoelectric myography sensors, one or more temperature sensors, one or more peripheral artery tonometry sensors, one or more photoplethysmography sensors, one or more pulse oximetry sensors, one or more moisture sensors, one or more pH sensors, one or more audio sensors, one or more force sensors, one or more light-emitting sensors, one or more light absorption sensors, one or more muscle movement sensors, one or more accelerometers, one or more heart rate monitors, and/or one or more capnography sensors.

In some embodiments, one or more sensors 2701 may be configured upon or within one or more portions of the therapeutic oral appliance 2700 at one or more locations that may facilitate the utility or functionality of the sensor(s) 2701. As a non-limiting example, one or more temperature sensors may be configured proximate to a deeper region within a user's oral cavity, such as at or near a distal end of the tongue retainer portion 2770 thereby allowing the temperature sensor(s) to obtain measurements closer to a core body region, thus increasing the accuracy of the measurements.

In some aspects, the therapeutic oral appliance 2700 may comprise one or more sensors 2701 that may comprise functionality that is at least partially dependent on emitting light and/or measuring light absorption, such as, for example and not limitation, one or more pulse oximetry sensors. By way of example and not limitation, such sensor(s) may be configured proximate to one or more thin membranes of a user's upper hard and/or soft palate by being located within or upon one or more portions of a superior surface of the therapeutic oral appliance 2700, such as the tongue retainer portion 2770 and/or the hard palate portion 2760.

In some aspects, the therapeutic oral appliance 2700 may comprise one or more sensors 2701 configured to measure one or more muscle movements within a user's mouth, throat, or oral cavity, wherein the sensor(s) 2701 may be positioned upon or within one or more portions of the tongue retainer portion 2770 to detect or measure any interactions between the therapeutic oral appliance 2700 and one or more portions of the user's tongue and/or soft palate.

In some implementations, one or more sensors 2701 may be configured to measure a user's bite force, wherein the sensor(s) 2701 may be located at or near one or more external or internal portions of the mouth guard portion 2750 of the therapeutic oral appliance 2700 to detect and measure an amount of force applied to the mouth guard portion 2750 when at least a portion of the mouth guard portion experiences physical contact from at least a portion of the user's upper teeth and at least a portion of the user's lower teeth in a substantially simultaneous manner. In some aspects, one or more sensors 2701 may be configured to detect or measure airway channel occlusion for a user, wherein such sensor(s) 2701 may be located at or near one or more internal or external portions of the mouth guard portion 2750 of the therapeutic oral appliance 2700.

In some aspects, the therapeutic oral appliance 2700 may comprise one or more materials that may facilitate the performance and functionality of the sensor(s) 2701. As a non-limiting example, the therapeutic oral appliance 2700 may at least partially comprise at least one optically transparent material so as not to interfere with the functioning of one or more sensors 2701 that may be at least partially dependent on producing, detecting, or measuring emitted and/or absorbed light, such as, by way of example and not limitation, one or more pulse oximetry sensors.

Figure 28A:
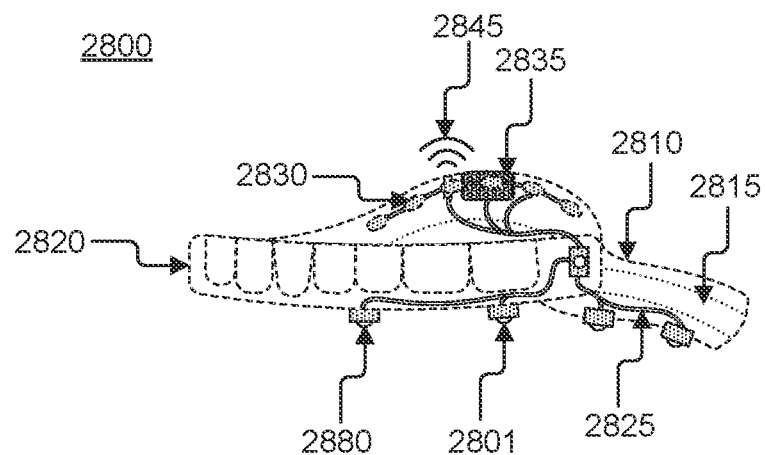
FIG. 28A illustrates an exemplary therapeutic oral appliance, according to some embodiments of the present disclosure.
Figure 28B:
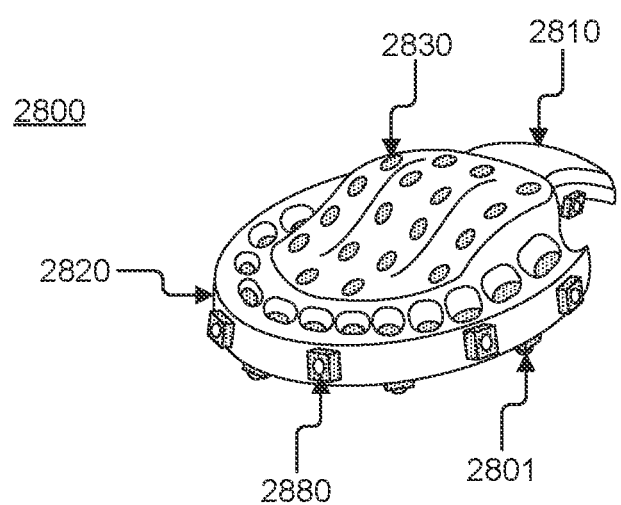
FIG. 28B illustrates a perspective view of an exemplary therapeutic oral appliance, according to some embodiments of the present disclosure.

Referring now to FIGS. 28A and 28B, an exemplary therapeutic oral appliance 2800, in accordance with some embodiments of the present disclosure, is illustrated. In some aspects, the therapeutic oral appliance 2800 may comprise one or more sensors 2801 and/or one or more electrodes 2880 configured within or upon one or more internal or external portions of a tongue retainer portion 2810, a mouth guard portion 2820, and/or a hard palate portion 2830 thereof In some embodiments, one or more electrical wires 2825 may be configured upon or embedded within one or more internal or external portions of the therapeutic oral appliance 2800. As a non-limiting example, one or more electrical wires 2825 may be embedded within one or more internal portions of the therapeutic oral appliance 2800 to block the electrical wire(s) 2825 from physically contacting one or more interior portions of a user's mouth.

In some embodiments, the electrical wire(s) 2825 may be attached to one or more sensors 2801, one or more electrodes 2880, at least one transmitting device 2845 (such as, for example and not limitation, an RF transmitter or Bluetooth® transmitter), at least one power source 2835 (such as, for example and not limitation, a battery), and/or at least one receiving device (such as, for example and not limitation, an RF receiver or a Bluetooth® receiver). In some implementations, the at least one transmitting device 2845 may comprise dual functionality in that it may also serve as a receiving device.

In some embodiments, the therapeutic oral appliance 2800 may transmit data obtained from one or more sensors 2801 and/or one or more electrodes 2880 to at least one external device, at least one wearable technology device, and/or at least one database or similar memory resource via the at least one transmitting device 2845. In some implementations, the performance or functionality of the one or more sensors 2801 and/or the one or more electrodes 2880 may be directed or altered by the at least one external device or the at least one wearable technology device via the at least one receiving device.

In some embodiments, by way of example and not limitation, the therapeutic oral appliance 2800 may comprise one or more sensors 2801 and/or one or more electrodes 2880 that may comprise at least one of: one or more electromyography electrodes, one or more acceleromyography sensors, one or more piezoelectric myography sensors, one or more temperature sensors, one or more peripheral artery tonometry sensors, one or more photoplethysmography sensors, one or more pulse oximetry sensors, one or more moisture sensors, one or more pH sensors, one or more audio sensors, one or more force sensors, one or more light-emitting sensors, one or more light absorption sensors, one or more muscle movement sensors, one or more heart rate monitors, and/or one or more capnography sensors.

In some embodiments, the therapeutic oral appliance 2800 may comprise one or more sensors 2801 and/or electrodes 2880 that may be configured upon or within one or more external or internal portions of the therapeutic oral appliance 2800 so as to optimize the performance or functionality of the sensor(s) 2801 and/or electrode(s) 2880. As a non-limiting example, one or more temperature sensors may be configured proximate to a deeper region within the oral cavity of a user, such as, for example and not limitation, by being positioned at or near the distal end of the tongue retainer portion 2810, thereby enabling the temperature sensor(s) to obtain measurements closer to the user's core body region, thus increasing the accuracy of the measurements.

By way of further example and not limitation, the therapeutic oral appliance 2800 may comprise one or more sensors 2801 that comprise functionality that is at least partially dependent on emitting light and/or measuring light absorption, such as, for example and not limitation, one or more pulse oximetry sensors. In some implementations, such sensor(s) 2801 may be located proximate to one or more thin membranes of one or more portions of a user's upper hard and/or soft palate by being positioned at or near one or more portions of a superior surface of the tongue retainer portion 2810 and/or the hard palate portion 2830 of the therapeutic oral appliance 2800.

In some aspects, the therapeutic oral appliance 2800 may comprise one or more sensors 2801 configured to measure one or more muscle movements within a user's mouth, throat, or oral cavity, wherein the sensor(s) 2801 may be configured upon or within one or more external or internal portions of the tongue retainer portion 2810 to detect and/or measure, by way of example and not limitation, one or more interactions between the therapeutic oral appliance 2800 and a user's tongue and/or soft palate. In some aspects, the therapeutic oral appliance 2800 may comprise one or more sensors 2801 configured to measure a user's bite force by being located at, upon, within, or proximate to one or more portions of the mouth guard portion 2820, or any other appropriate portion of the therapeutic oral appliance 2800. In some aspects, the therapeutic oral appliance 2800 may comprise one or more sensors 2801 configured to detect and/or measure at least partial airway channel occlusion for a user by being configured, by way of example and not limitation, within, upon, or proximate to one or more internal or external portions of the mouth guard portion 2820 of the therapeutic oral appliance 2800.

In some aspects, the therapeutic oral appliance 2800 may comprise at least one material that may facilitate the functionality and/or performance of the sensor(s) 2801 and/or electrode(s) 2880. As a non-limiting example, the therapeutic oral appliance 2800 may at least partially comprise at least one optically transparent material to minimize potential interference of the functioning of at least one pulse oximetry sensor.

In some embodiments, the therapeutic oral appliance 2800 may comprise one or more electrodes 2880 configured to facilitate transcutaneous electrical nerve and/or electrical muscle stimulation. As a non-limiting example, one or more electrodes 2880 may be configured within, upon, or proximate to one or more portions of an interior and/or superior surface of the therapeutic oral appliance 2800 to help strengthen and tone one or more upper airway dilator muscles and/or tongue muscles of a user. In some aspects, one or more electrodes 2880 may at least partially comprise and/or be at least partially configured within one or more electrically conductive materials. In some aspects, by way of example and not limitation, one or more electrodes 2880 may at least partially comprise and/or may be at least partially configured within at least one material that comprises one or more of: carbon-infused medical grade silicone rubber, one or more carbon nanotube silicone composites, PDMS, or one or more PDMS composites, including those used in combination with nickel, carbon nanotubes, and/or silver.

In some embodiments, one or more portions of the tongue retainer portion 2810, such as, for example and not limitation, at least one airway 2815 may comprise one or more electronic components. For example, the therapeutic oral appliance 2800 may comprise one or more electrodes 2880 that may be configured to provide transcutaneous electrical stimulation to one or more oropharyngeal and/or tongue muscles of a user. In some aspects, such stimulation may facilitate an increase in muscle tone, thereby promoting opening of a user's oral airway channel.

In some aspects, the therapeutic oral appliance 2800 may comprise one or more electrodes 2880 configured to facilitate neuromuscular electrical stimulation. By way of example and not limitation, such neuromuscular electrical stimulation may be implemented in conjunction with one or more sensors 2801 in the form of capnography sensors, respiratory sensors, thoracic sensors, and/or other breathing sensors. In some embodiments, when one or more of these sensors 2801 may detect that a user is not breathing or that the user's breathing is at least partially obstructed, the one or more neuromuscular electrical stimulation electrodes 2880 may be configured to send at least one electrical pulse that may cause the user's tongue and/or upper airway dilator muscles to at least partially contract to facilitate opening of the user's airway passage.

In some implementations, the therapeutic oral appliance 2800 may be used to alleviate one or more health concerns for a user, such as sleep apnea. In some aspects, neuromuscular electrical stimulation provided by one or more electrodes 2880 of the therapeutic oral appliance 2800 may facilitate an increase in muscle tone within the user's mouth, oral cavity, or throat, thereby reducing sleep apnea symptoms. In some non-limiting exemplary embodiments, this increase in muscle tone may allow the size of the center portion (or web) of the airway channel 2815 and/or a cross section of the tongue retainer portion 2810 to be incrementally and gradually decreased overtime, such as, for example and not limitation, by being compressed or compacted in an adjustable manner, by being replaced by a succession of one or more modular components, or by using a plurality of therapeutic oral appliances 2800 of different sizes. By way of example and not limitation, the gradual reduction of the size of the center portion of the airway channel 2815 or the tongue retainer portion 2810 may result in increased user comfort.

In some embodiments, one or more electrodes 2880 for facilitating neuromuscular electrical stimulation may be configured within or upon one or more portions of the therapeutic oral appliance 2800 at a location that may be advantageous to its purpose or functionality, which may be to assist a user in overcoming sleep apnea, as a non-limiting example. In some aspects, one or more neuromuscular electrical stimulation electrodes 2880 may be located on any portion(s) of the therapeutic oral appliance 2800 that may at least partially contact a user's tongue, such as, for example and not limitation, the tongue retainer portion 2810. By way of example and not limitation, at least one neuromuscular electrical stimulation electrode 2880 may be placed upon or near the user's chin to facilitate stimulation of the genio-glossus muscle. As a non-limiting example, the simulation of the genioglossus muscle may cause the tongue to tighten and at least partially protrude from the user's mouth, thereby increasing the opening of the user's airway channel. In some aspects, this direct stimulation of the genioglossus muscle may produce an effect similar to that facilitated by hypoglossal nerve stimulators without the need for any surgical implants.

Figure 29:
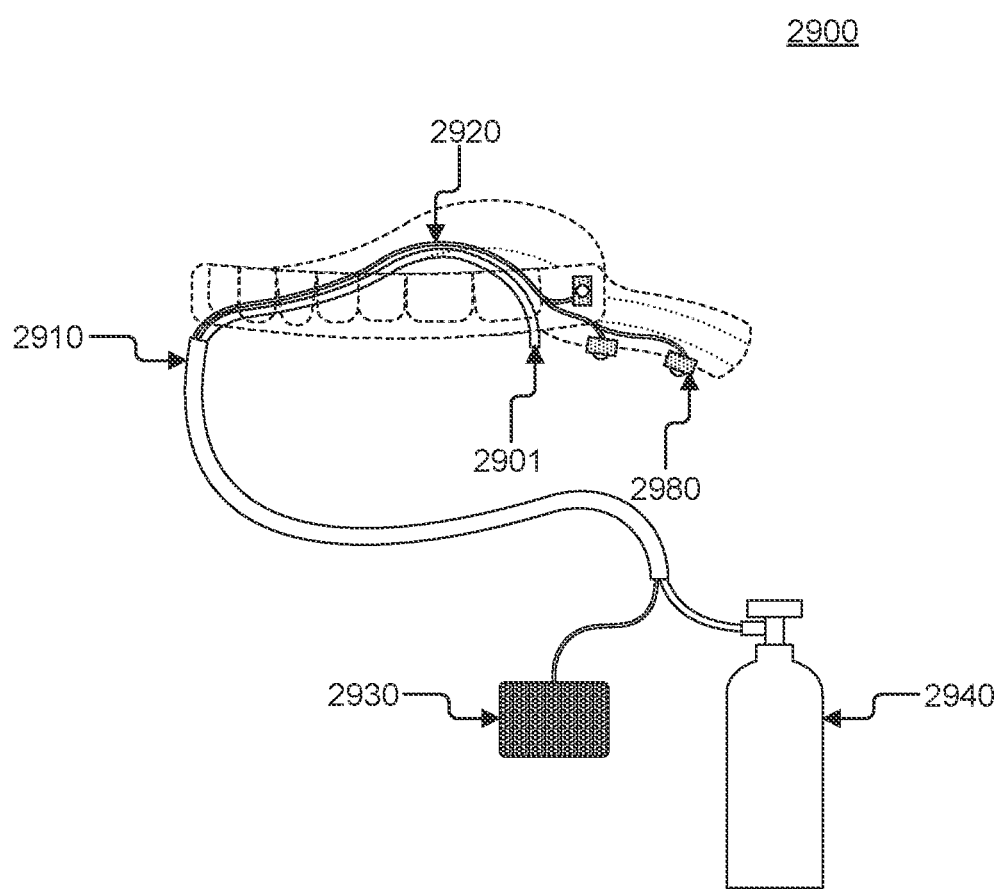
FIG. 29 illustrates a perspective view of an exemplary therapeutic oral appliance, according to some embodiments of the present disclosure.

Referring now to FIG. 29, a perspective view of an exemplary therapeutic oral appliance 2900, according to some embodiments of the present disclosure, is illustrated. In some aspects, the therapeutic oral appliance 2900 may comprise at least one amount of substantially hollow tubing 2910. In some non-limiting exemplary embodiments, the hollow tubing 2910 may be used to measure airflow being inhaled or exhaled by a user. In some aspects, the hollow tubing 2910 may be used to at least partially encapsulate one or more electrical wires 2920. In some aspects, the electrical wire(s) 2920 may be removably or securely attached to one or more sensors 2901 and/or one or more electrodes 2980.

In some aspects, the hollow tubing 2910 may be attached to or integrated with one or more gas flow meters and/or one or more gas analyzers, such as, for example and not limitation, one or more air flow meters, one or more capnography devices, and/or one or more oxygen analyzers 2930 in order to measure one or more aspects of the gases 2940 flowing into or out of a user's body. In some implementations, the hollow tubing 2910 may be used to deliver one or more gasses 2940, including but not limited to, supplemental oxygen, nitric oxide, and/or humidification to a user. In some embodiments, the hollow tubing 2910 may be used to deliver one or more medicated gases 2940 to a user, such as, for example and not limitation, one or more aerosolized or nebulized medications within one or more gases 2940 in the form of air or oxygen.

Conclusion

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A therapeutic oral appliance comprising:
a mouth guard portion, wherein the mouth guard portion is configured to at least partially interface with one or more teeth of a user;
a hard palate portion configured to at least partially interface with a hard palate of a mouth of the user, wherein the hard palate portion extends upward from the mouth guard portion; and
at least one of: at least one sensor and at least one electrode, wherein the at least one sensor or at least one electrode is configured upon the therapeutic oral appliance; and one or more electrical wires configured to connect the at least one sensor and at least one electrode to the therapeutic oral appliance, wherein the one or more electrical wires are embedded within the therapeutic oral appliance to avoid contacting one or more interior portions of a user's mouth; and
a tongue retainer portion, wherein the tongue retainer portion extends from the hard palate portion into at least a portion of a throat of the user, wherein the tongue retainer portion comprises an upper surface, a lower surface, two opposing sidewalls, and a longitudinal length, at least one airway, wherein the at least one airway comprises one or more indentations recesses within each of the two sidewalls of the tongue retainer portion, wherein the at least one airway extends along at least a portion of the longitudinal length of the tongue retainer portion, wherein the at least one airway comprises an air flow pathway that follows a natural anatomical airway passage of the user.

2. The therapeutic oral appliance of claim 1, wherein the tongue retainer portion is fixed to a distal end of the hard palate portion.

3. The therapeutic oral appliance of claim 1, wherein the mouth guard portion comprises a universal fit that may be used by a generic user.

4. The therapeutic oral appliance of claim 1, wherein the at least one electrical wire is configured upon one or more external surfaces of the therapeutic oral appliance.

5. The therapeutic oral appliance of claim 1, wherein the tongue retainer portion extends directly from the hard palate portion into the at least a portion of the throat of the user.

6. The therapeutic oral appliance of claim 1, wherein a cross section of the tongue retainer portion substantially comprises an I-beam structure.

7. The therapeutic oral appliance of claim 1, wherein the therapeutic oral appliance at least partially comprises at least one silicone material.

8. The therapeutic oral appliance of claim 1, wherein the therapeutic oral appliance at least partially comprises at least one material that comprises a low shore hardness.

9. The therapeutic oral appliance of claim 1, wherein the therapeutic oral appliance comprises at least one material that becomes pliable when exposed to heat.

10. The therapeutic oral appliance of claim 1, wherein the at least one airway originates and extends from a top portion of the mouth guard portion.

11. The therapeutic oral appliance of claim 1, wherein the therapeutic oral appliance at least partially comprises at least one optically transparent material.

12. The therapeutic oral appliance of claim 1, wherein the at least one of: the at least one sensor and the at least one electrode comprises at least one of: at least one electromyography electrode, at least one acceleromyography sensor, at least one piezoelectric myography sensors, at least one temperature sensor, at least one peripheral artery tonometry sensor, at least one one photoplethysmography sensor, at least one pulse oximetry sensor, at least one moisture sensor, at least one pH sensor, at least one audio sensor, at least one force sensor, at least one light-emitting sensor, at least one light absorption sensor, at least one muscle movement sensor, at least one accelerometer, at least one heart rate monitor, and at least one capnography sensor.

13. The therapeutic oral appliance of claim 1, wherein the therapeutic oral appliance further comprises at least one transmitting device.

14. The therapeutic oral appliance of claim 13, wherein the at least one transmitting device is configured to transmit data obtained from the at least one of: the at least one sensor and the at least one electrode.

15. The therapeutic oral appliance of claim 14, wherein data obtained from the at least one of: the at least one sensor and the at least one electrode is transmitted to at least one database for storage.

16. The therapeutic oral appliance of claim 1, wherein the therapeutic oral appliance further comprises at least one power source.

* * * * *